(12) United States Patent
Wu et al.

(10) Patent No.: US 6,241,663 B1
(45) Date of Patent: Jun. 5, 2001

(54) METHOD FOR IMPROVING NON-INVASIVE DETERMINATION OF THE CONCENTRATION OF ANALYTES IN A BIOLOGICAL SAMPLE

(75) Inventors: Xiaomao Wu, Gurnee; Omar S. Khalil, Libertyville; Tzyy-Wen Jeng, Vernon Hills; Shu-Jen Yeh, Grayslake; Charles F. Hanna, Libertyville, all of IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/302,207

(22) Filed: Apr. 29, 1999

Related U.S. Application Data

(63) Continuation-in-part of application No. 09/080,470, filed on May 18, 1998.

(51) Int. Cl.[7] ..................................................... A61B 5/00
(52) U.S. Cl. ........................................... 600/310; 600/322
(58) Field of Search ..................................... 600/310, 322, 600/323, 326, 334, 344, 473; 356/39, 41; 250/341.1, 341.2, 341.5, 341.6, 339.03, 339.09

(56) References Cited

U.S. PATENT DOCUMENTS 3,628,525    12/1971    Polanyi et al. .

(List continued on next page.)

FOREIGN PATENT DOCUMENTS 42 42 083    6/1994    (DE) .

(List continued on next page.)

OTHER PUBLICATIONS

Applied Optics, vol. 31, No. 10, Apr. 1, 1992, pp. 1346–1398.

(List continued on next page.)

*Primary Examiner*—Eric E. Winakur
(74) *Attorney, Agent, or Firm*—David L. Weinstein

(57) ABSTRACT

A method for determining the concentration of an analyte in a biological sample comprising the steps of:

(1) providing an optical measuring instrument that comprises at least one thermally controllable optical measuring element that comes into contact with the surface of the biological sample;

(2) applying an inert, thermally conductive, optically transparent coupling agent to the at least one optical measuring element or to the surface of the biological sample or both so that the coupling agent will be disposed at the interface of the surface of the biological sample and the at least one optical measuring element;

(3) measuring optical properties of the biological sample by means of the optical measuring instrument; and (4) correlating the optical properties of the biological sample with the concentration of the analyte in the biological sample.

A coupling agent suitable for this invention must have several properties to enable it to help decrease measurement variation, especially drift. One of the most important properties is sufficiently high optical stability that the optical properties of the coupling agent do not change even during prolonged experiments, such as oral glucose tolerance tests. Secondly, the coupling agent should have sufficiently high thermal conductivity to allow fast, efficient heat transfer between the optical probe and the biological sample. Third, the coupling agent should have sufficiently high viscosity to prevent it from migrating from the measurement area. Yet, it should also have sufficiently low viscosity to allow sufficient contact between the optical probe and the biological sample and to permeate into any small pockets between the probe and the biological sample that would otherwise be filled with the air. Fourth, the coupling agent should be inert. Material from the coupling agent should not diffuse into the biological sample and material from the biological sample should not diffuse into the coupling agent.

22 Claims, 15 Drawing Sheets

U.S. PATENT DOCUMENTS

| | | |
|---|---|---|
| 3,638,640 | 2/1972 | Shaw . |
| 4,223,680 | 9/1980 | Jobsis . |
| 4,259,963 | 4/1981 | Huch . |
| 4,432,365 | 2/1984 | Leist . |
| 4,655,225 | 4/1987 | Dähne et al. . |
| 4,882,492 | 11/1989 | Schlager . |
| 4,890,619 | 1/1990 | Hatschek . |
| 4,926,867 | 5/1990 | Kanda et al. . |
| 4,975,581 | 12/1990 | Robinson et al. . |
| 5,007,423 | 4/1991 | Branstetter et al. . |
| 5,057,695 | 10/1991 | Hirao et al. . |
| 5,086,229 | 2/1992 | Rosenthal et al. . |
| 5,115,133 | 5/1992 | Knudson . |
| 5,122,974 | 6/1992 | Chance . |
| 5,131,391 | 7/1992 | Sakai et al. . |
| 5,148,082 | 9/1992 | Itou et al. . |
| 5,187,672 | 2/1993 | Chance et al. . |
| 5,209,231 | 5/1993 | Cote et al. . |
| 5,218,207 | 6/1993 | Rosenthal . |
| 5,237,178 | 8/1993 | Rosenthal et al. . |
| 5,277,181 | 1/1994 | Mendelson et al. . |
| 5,297,548 | 3/1994 | Pologe . |
| 5,313,941 | 5/1994 | Braig et al. . |
| 5,321,265 | 6/1994 | Block . |
| 5,324,979 | 6/1994 | Rosenthal . |
| 5,337,745 | 8/1994 | Benaron . |
| 5,348,002 | 9/1994 | Caro . |
| 5,348,003 | 9/1994 | Caro . |
| 5,361,758 | 11/1994 | Hall et al. . |
| 5,362,966 | 11/1994 | Rosenthal et al. . |
| 5,372,136 | 12/1994 | Steuer et al. . |
| 5,379,764 | 1/1995 | Barnes et al. . |
| 5,383,452 | 1/1995 | Buchert . |
| 5,402,778 | 4/1995 | Chance . |
| 5,452,716 | 9/1995 | Clift . |
| 5,481,113 | 1/1996 | Dou et al. . |
| 5,492,118 | 2/1996 | Gratton et al. . |
| 5,492,769 | 2/1996 | Pryor et al. . |
| 5,497,769 | 3/1996 | Gratton et al. . |
| 5,499,627 | 3/1996 | Steuer et al. . |
| 5,515,847 | 5/1996 | Braig et al. . |
| 5,533,509 | 7/1996 | Koashi et al. . |
| 5,551,422 | 9/1996 | Simonsen et al. . |
| 5,553,615 | 9/1996 | Carim et al. . |
| 5,553,616 | 9/1996 | Ham et al. . |
| 5,596,987 | 1/1997 | Chance . |
| 5,665,530 | 9/1997 | Oyamada et al. . |
| 5,672,875 | 9/1997 | Block et al. . |
| 5,676,143 | 10/1997 | Simonsen et al. . |
| 5,720,284 | 2/1998 | Aoyagi et al. . |
| 5,770,454 | 6/1998 | Essenpreis et al. . |
| 5,823,951 | 10/1998 | Messerschmidt . |
| 5,978,691 * | 11/1999 | Mills .................................. 600/334 |

FOREIGN PATENT DOCUMENTS

| | | |
|---|---|---|
| 44 17 639 | 11/1995 | (DE) . |
| 196 34 152 | 3/1998 | (DE) . |
| 0 472 216 | 2/1992 | (EP) . |
| 0 810 429 | 12/1997 | (EP) . |
| 92/10131 | 6/1992 | (WO) . |
| 92/20273 | 11/1992 | (WO) . |
| 93/07801 | 4/1993 | (WO) . |
| 93/13706 | 7/1993 | (WO) . |
| 94/02837 | 2/1994 | (WO) . |
| 94/05984 | 3/1994 | (WO) . |
| 94/13199 | 6/1994 | (WO) . |
| 95/20757 | 8/1995 | (WO) . |
| 98/03847 | 1/1998 | (WO) . |
| 99/59464 | 11/1999 | (WO) . |

OTHER PUBLICATIONS

Bruulsema, et al., "Correlation between blood glucose concentration in diabetics and noninvasively measured tissue optical scattering coefficient", Optics Letters, vol. 22, No. 3, 1997, pp. 190–192.

Heinemann, et al., "Non–invasive continuous glucose monitoring in Type I diabetic patients with optical glucose sensors", Diabetologia, vol. 41, 1998, pp. 848–854.

Kienle, et al. "Spatially resolved absolute diffuse reflectance measurements for noninvasive determination of the optical scattering and absorption coefficients of biological tissue", Applied Optics, vol. 35, No. 13, 1996, pp. 2304–2314.

Marbach, et al., "Noninvasive Blood Glucose Assay by Near–Infrared Diffuse Reflectance Spectroscopy of the Human Inner Lip", Applied Spectroscopy, vol. 47, No. 7, 1993, pp. 875–881.

Qu, et al., "Monte Carlo Modeling Studies of the Effect of Physiological Factors and other Analytes on the Determination of glucose Concentration In vivo by Near Infrared Optical Absorption and Scattering Measurements", Journal of Biomedical Optics, vol. 2, No. 3, (1997), pp. 319–325.

Quan, et al., "Glucose determination by a pulsed photoacoustic technique: an experimental study using a gelatin–based tissue phantom", Phys. Med. Biol., vol. 38 (1993) pp. 1911–1922.

Robbins, et al., "The Endocrine Pancreas", Pathologic Basis of Disease, $3^{rd}$ Edition, W. B. Saunders Company (1984), pp. 972–990.

Tooke, et al., "Skin Microvascular Blood Flow Control in Long Duration Diabetics with and without Complications", Diabetes Research, No. 5, 1987, pp. 189–192.

Wilson, et al, "Progress toward the Development of an Implantable Sensor for Glucose", Clinical Chemistry, vol. 38, No. 9, 1992, pp. 1613–1617.

R. Graaff, et al., "Reduced light–scattering properties for mixtures of spherical particles: a simple approximation derived from Mie calculations", Applied Optics, vol. 31, No. 10, Apr. 1, 1992, pp. 1370–1376.

Jobsis, "Noninvasive, Infrared Monitoring of Cerebral and Myocardial Oxygen Sufficiency and Circulatory Parameters", Science, vol. 198, 1977, pp. 1264–1267.

Gopinath, et al., "Near–infrared spectroscopic localization of intracranial hematomas", Journal of Neurosurgery, vol. 79, 1993, pp. 43–47.

Zhang, et al., "Investigation of Noninvasive in Vivo Blood Hematocrit Measurement Using NIR Reflectance Spectroscopy and Partial Least–Squares Regression", Applied Spectroscopy, vol. 54, No. 2, 2000, pp. 294–299.

Lin, et al., "Dynamics of tissue optics during laser heating of turbid media", Applied Optics, vol. 35, No. 19, 1996, pp. 3413–3420.

Laufer, et al., "Effect of temperature on the optical properties of ex vivo human dermis and subdermis", Phys. Med. Biol., vol. 43, 1998, pp. 2479–2489.

Bruulsema, et al., "Optical Properties of Phantoms and Tissue Measured in vivo from 0.9–1.3 μm using Spatially Resolved Diffuse Reflectance", SPIE Proceedings, vol. 2979, 1997, pp. 325–334.

T. Shiga, et al., "Study of an Algorithm Based on Model Experiments and Diffusion Theory for a Portable Tissue Oximeter", Journal of Biomedical Optics, vol. 2, No. 2, Apr. 1997, pp. 154–161.

Jacques, et al., "Monte Carlo Modeling of Light Transport in Tissues", *Optical–Thermal Response of Laser–Irradiated Tissue,* edited by A.J. Welch and M.J.C. van Gemert, Plenum Press, New York, 1995, pp. 73–100.

Wilson, "Measurement of Tissue Optical Properties: Methods and Theories", *Optical–Thermal Response of Laser–Irradiated Tissue,* edited by A.J. Welch and M.J.C. van Gemert, Plenum Press, New York, 1995, pp. 233–274.

Morris, et al., "Basic Examination of Blood", *Clinical Diagnosis and Management by Laboratory,* 1996, pp. 549–559.

Lin, et al., "Dynamics of tissue reflectance and transmittance during laser irradiation", SPIE Proceedings, vol. 2134A Laser–Tissue Interaction V, 1994, pp. 296–303.

* cited by examiner

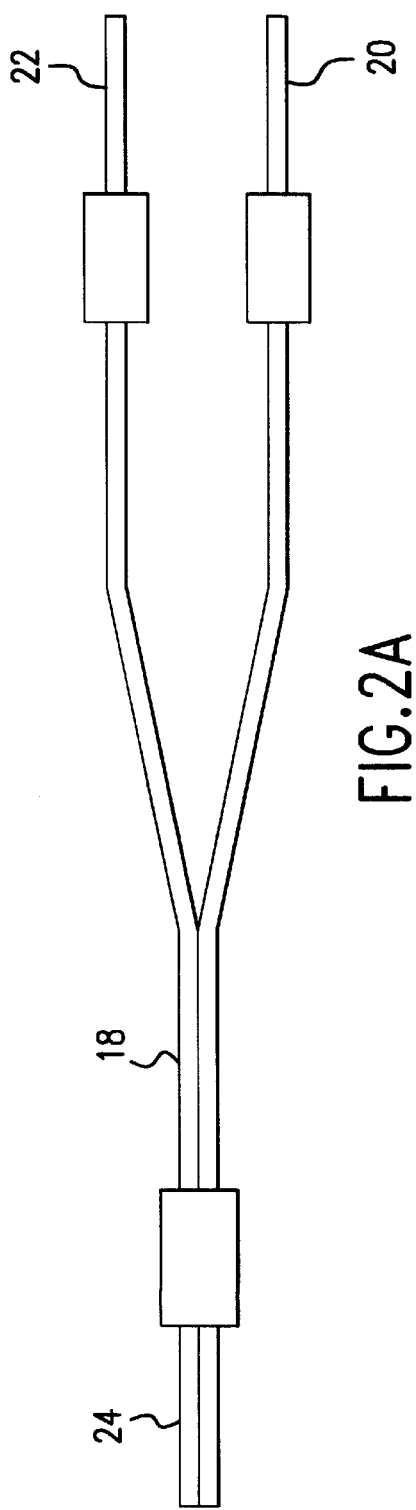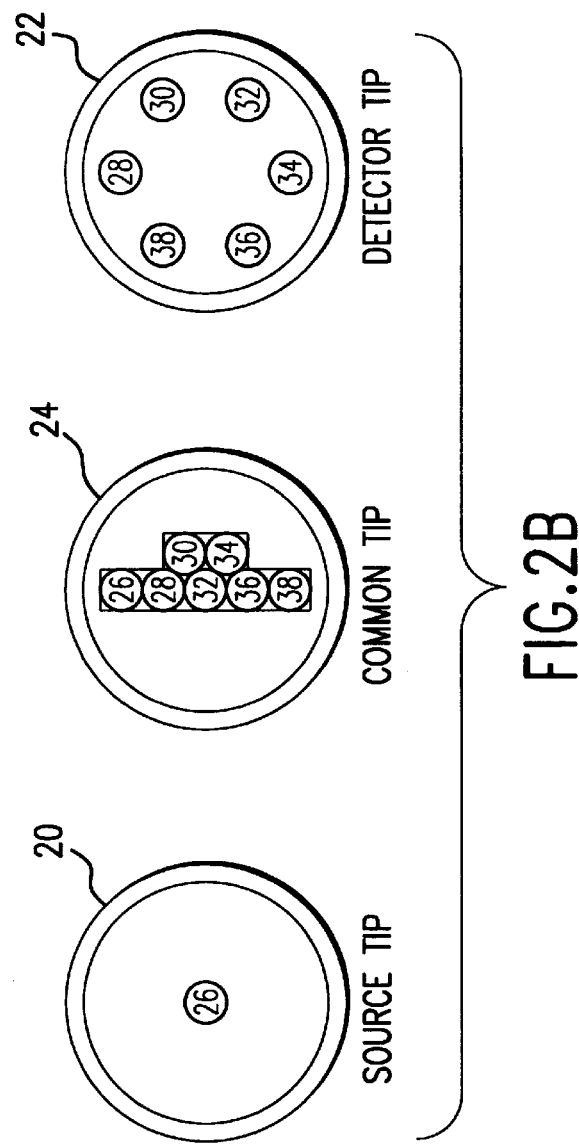
FIG.2A
FIG.2B

METHOD FOR IMPROVING NON-INVASIVE DETERMINATION OF THE CONCENTRATION OF ANALYTES IN A BIOLOGICAL SAMPLE

This application is a continuation-in-part of co-pending U.S. patent application Ser. No. 09/080,470, filed May 18, 1998, assigned to the assignee of this application.

BACKGROUND OF THE INVENTION

1. Field of the Invention

This invention relates to a method for improving non-invasive determination of the concentration of an analyte in a human tissue, and, more particularly, a method for improving non-invasive determination of the concentration of analytes in human tissues and human body parts by applying a coupling agent at the interface between an optical measurement device and the surface of a tissue of a human.

2. Discussion of the Art

Non-invasive determination of the concentration of an analyte in a biological sample, e. g., glucose in human tissue, has been attempted by several methods. Optical methods employing infrared radiation operate on the basis that light can penetrate the tissue and then provide an absorption or scattering measurement. These methods involve the steps of introducing light and collecting light by means of optical devices having elements in contact with the skin.

Robinson et al., U.S. Pat. No. 4,975,581, describes a method for the non-invasive measurement of the concentration of glucose by detecting diffusely reflected light having a wavelength in the near infrared region of the electromagnetic spectrum. Barnes et al., U.S. Pat. No. 5,379,764, describes a method for the non-invasive measurement of the concentration of glucose via light having a wavelength in the near infrared region of the electromagnetic spectrum. The interface between the optical measurement device and the surface of the skin is formed by contacting the surface of the skin with the optical measurement device. Dahne et al., U.S. Pat. No. 4,655,225, describes an optical system for in vivo measurement of the concentration of glucose. In this system, light is transmitted from an optical element to the skin and from the skin to the optical element through the air. Caro, U.S. Pat. No. 5,348,003, describes the use of temporarily modulated electromagnetic energy for the measurement of the concentration of glucose and other analytes, but a portion of the light energy is propagated through the air to the surface of the skin and reflected back from the skin.

Marbach, "Measurement Techniques for IR Spectroscopic Blood Glucose Determination", published in 1993, and R. Marbach, T. H. Koschinsky, F. A. Gries, and H. M. Heise, "Noninvasive Blood Glucose Assay by Near-Infrared Diffuse Reflectance Spectroscopy of the Human Inner Lip", APPLIED SPECTROSCOPY, Vol. 47, 1993, pp. 875–881, describe an optical accessory for carrying out measurements of diffuse reflectance on a human lip. That accessory suppresses the insensitivity to Fresnel or specular reflection on the skin surface area by matching the refractive index of the optical accessory to that of tissue. Calcium fluoride ($CaF_2$) was disclosed as the material for constructing the optical accessory. Calcium fluoride is not an ideal index match to tissue, having an index of 1.42, relative to that of tissue, at approximately 1.38. Thus, an index mismatch occurs at the accessory to tissue interface assuming complete contact between the accessory and the tissue. The optical efficiency of the accessory is further compromised by the fact that the accessory and the tissue will not make perfect optical contact due to roughness of the surface of the tissue. The result is a significant refractive index mismatch where light is forced to travel from the accessory (refractive index=1.42) to air (refractive index=1.0) and then to tissue (refractive index=1.38). Thus, the inherent roughness of tissue results in small air gaps between the accessory and the tissue, which decrease the optical throughput of the system, and subsequently compromise the performance of the measurement accessory.

Simonsen et al., U.S. Pat. No. 5,551,422, describes a method for the determination of the scattering coefficient in tissue based on spatially resolved diffuse reflectance. A clinical apparatus and a method based on this patent employ a double-stick tape to affix the optical probe to the surface of the skin. This interface material is used for mechanical attachment purpose and does not address problems relating to measurement variations. J. T. Bruulsema, et al, "Correlation between blood glucose concentration in diabetics and noninvasively measured tissue optical scattering coefficient", OPTICS LETTERS, Vol. 22, 1997, pp.190–192 (hereinafter "Bruulsema, et al."), describe a clinical study based on the method of Simonsen et al., U.S. Pat. No. 5,551,422. Another clinical study was reported by L. Heinemann, et al., "Non-invasive continuous glucose monitoring in Type I diabetic patients with optical glucose sensors", Diabetologia, Vol. 41, 1998, pp. 848–854. In both studies significant drift in the optical measurement was observed, leading to changes in the scattering coefficient independent of changes in glucose concentration and lack of correlation between changes in the scattering coefficient and changes in glucose concentration. The poor quality of the data did not allow the use of statistical analysis to correlate or predict the concentration of glucose.

The use of optical coupling agents for improving contrast and image quality in microscopic examinations is known in the art. In a classical example, immersion oil has been applied to the interface between a microscope lens and the sample object. The use of optical matching fluids to improve the precision of optical measurements is also known in the art. The use of an optical matching fluid that has the same refractive index as that of the object to be measured decreases reflection losses at the surface and improves measurement precision and accuracy.

Chance, U.S. Pat. No. 5,596,987 and Chance, U.S. Pat. No. 5,402,778, describe methods for measuring optical properties of tissue. In particular, U.S. Pat. No. 5,596,987 discloses a spectrophotometric system including a spectrophotometer with an optical input port adapted to introduce radiation into an object and an optical detection port adapted to detect radiation that has migrated through a path in the object, photon escape preventing means arranged around the object, which is relatively small, and adapted to limit escape of the introduced photons outside the object, and processing means adapted to determine an optical property of the object based on the changes between the introduced and the detected radiation. The system also includes an optical medium of a relatively large volume, forming photon escape preventing means, having selectable scattering and absorptive properties, positioning means adapted to locate the biological tissue of interest into the migration path to create a tissue-medium optical path, the optical medium substantially limiting escape of photons from the tissue-medium optical path, and processing means adapted to determine a physiological property of the tissue based on the detected optical property of the tissue-medium optical path and the scattering or absorptive properties of the optical medium. The photon escape preventing means includes an optical medium of a selectable optical property surrounding the object. The selectable optical property is an absorption or scattering coefficient. The medium has at least one optical property matched to the optical property of the object. The optical coupling system includes an optical matching fluid that is contained within a flexible, optically transparent bag and disposed partially around the monitored tissue and the excitation and detection ports of the system. The optical medium may include scattering material, such as solid particles having smooth, spherical surfaces, or styrofoam. The optical medium may include a liquid having selectable absorptive or scattering properties, such as an Intralipid solution. The optical coupling medium may include a pliable solid having selectable scattering or absorption properties. The spectrophotometric system employing such an optical medium allows one to locate tumors having optical properties different from those of normal tissue.

Messerschmidt, U.S. Pat. Nos. 5,655,530 and 5,823,951, describes an optical method for measuring a blood analyte in human tissue non-invasively. Specifically, these patents disclose disposing an index-matching medium between a sensor element and a sample area on a skin surface. The method of measurement described in these patents requires detecting a mixture of diffuse and specular reflection. The use of an index-matching medium decreases the specular reflection component that is attributable to Fresnel reflections at glass/ air/tissue interfaces. Two types of index-matching media were described, hydrophobic refractive index matching fluids and hydrophobic refractive index matching fluids containing a hydrophilic additive.

Co-pending U.S. application Ser. No. 09/080,470, filed May 18, 1998, assigned to the assignee of this application, describes a non-invasive glucose sensor employing a temperature control. One purpose of controlling the temperature is to minimize the effect of physiological variables. Co-pending U.S. application Ser. No. 09/098,049, filed Nov. 23, 1998, assigned to the assignee of this application, describes methods for determining optical properties of tissue having more than one layer. The methods involve the use of a plurality of groups of closely spaced optical fibers that are located at spatially resolved measurement sites. Each group yields information relating to a specific layer in the sample. The selection of a particular layer for which the optical property is determined depends on the distance between the light illumination site and the site of the group of detecting elements. The layers described in the co-pending application are within the depth of 3 mm for samples of human tissue. In body parts having a thin layer of skin, such as the forearm or the abdomen, this depth encompasses the stratum corneum, the epidermis, and the dermis. Both applications teach the use of a temperature controlled optical element that is brought in contact with the skin.

Although a variety of spectroscopic techniques have been disclosed in the art, there is still no commercially available device that provides non-invasive measurements of glucose concentration with an accuracy that is comparable to that of invasive methods, i. e., analysis of glucose in blood withdrawn from human body parts. Also, spectroscopic techniques in the prior art fail to address the effect of variations in efficiency of optical coupling between the measuring device and the skin. These variations result in drift of the measurement induced by the measuring device. As a result, current approaches to non-invasive metabolite testing, such as glucose monitoring, have not achieved acceptable precision and accuracy.

Calibration of an optical instrument for non-invasive glucose measurements can be achieved by performing a meal tolerance test or an oral glucose tolerance test. A test subject ingests a given amount of food or drink after fasting for several hours. As a result of such ingestion, the glucose concentration in the blood of the test subject will change. The concentration of glucose in blood can be determined by a conventional prior art invasive procedure, such as that involving collection of blood by means of a finger stick and determination of blood glucose level via a disposable test strip and an optical or electrochemical detector. The signal from the non-invasive optical instrument is processed and is correlated with the glucose concentration determined at the same time by the invasive procedure. The resultant plot of data collected by means of the non-invasive procedure vs. data collected by means of the invasive procedure is a calibration curve, which can be obtained by the use of any appropriate fitting method, such as linear least squares fitting.

Touching the optical measuring probe to the skin leads to a unidirectional change in signal as a function of time, even in the absence of changes in glucose concentration. The temporal behavior reported by J. T. Bruulsema, et al. provided an example of such variations. This change in signal as a function of time, independent of changes in concentration of analytes in the sample, is called drift.

Robinson, et al. (U.S. Pat. No. 4,975,581) observed such a drift and used the first derivative of the spectrum to minimize it. This compensation, however, does not address the cause of the problem. In fact, in the spatially resolved diffuse reflectance measurement at the skin, drift of signal observed by Bruulsema, et al. was so large that it precluded statistical analysis of the results.

SUMMARY OF THE INVENTION

In one aspect, this invention provides a method for determining the concentration of an analyte in a biological sample comprising the steps of:

(1) providing an optical measuring instrument that comprises at least one thermally controllable optical measuring element that comes into contact with the surface of the biological sample;

(2) applying an inert, thermally conductive, optically transparent coupling agent to the at least one optical measuring element or to the surface of the biological sample or both so that the coupling agent will be disposed at the interface of the surface of the biological sample and the at least one optical measuring element;

(3) measuring optical properties of the biological sample by means of the at least one optical measuring instrument; and (4) correlating the optical properties of the biological sample with the concentration of an analyte in the biological sample.

In another aspect, this invention provides a method for calibrating an optical instrument for a non-invasive optical measurement from a tissue of a body part comprising the steps of:

(1) providing an optical measuring instrument that comprises at least one thermally controllable optical measuring element that comes into contact with the surface of the tissue;

(2) applying an inert, thermally conductive, optically transparent coupling agent to the at least one optical measuring element or to the surface of the tissue or both so that the coupling agent will be disposed at the interface of the surface of the tissue and the at least one optical measuring element;

(3) inducing a change in the concentration of the analyte in the tissue over a defined period of time;

(4) measuring the change in at least one optical property of the tissue by means of the at least one optical measuring element during the defined period of time;

(5) determining the change in the concentration of the analyte in the tissue by means of a reference method that involves taking a sample from the tissue for analysis during the defined period of time;

(6) correlating the change in the at least one optical property of the tissue with the change in the concentration of the analyte in the tissue to derive calibration data; and (7) using the calibration data to determine the concentration of the analyte in the tissue.

A coupling agent suitable for this invention must have several properties to enable it to help decrease measurement variation, especially drift. One of the most important properties is sufficiently high optical stability that the optical properties of the coupling agent do not change even during prolonged experiments, such as meal tolerance tests and oral glucose tolerance tests, which tests typically extend over a period of several hours. The optical properties of the coupling agent should also remain stable during storage. Thus, hygroscopic agents, such as glycerol, are not suitable as coupling agents for this invention, because they absorb water from the biological sample, e. g., human tissue, and the atmosphere, which causes their physical properties to change over time.

Secondly, the coupling agent should have sufficiently high thermal conductivity to allow fast, efficient heat transfer between the optical probe and the biological sample, e. g., human tissue. The thermal conductivity of the coupling agent should be at least four times that of air, i. e., greater than 1 miliwatt/cm/° C.

Third, the coupling agent should have sufficiently high viscosity to prevent it from migrating from the measurement area. Yet, it should also have sufficiently low viscosity to allow sufficient contact between the optical probe and the biological sample, e. g., human tissue, and to permeate into any small pockets between the probe and the biological sample that would otherwise be filled with the air. The preferred viscosity of the coupling agent ranges from about 10 centipoises to about 100,000 centipoises.

Fourth, the coupling agent should be inert. Material from the coupling agent should not diffuse into the biological sample and material from the biological sample should not diffuse into the coupling agent. Thus, coupling agents containing a high concentration of water or alcohol are not suitable for this invention. Low molecular weight compounds, such as water or alcohol, can diffuse through the biological sample during the period of measurement, thereby causing a change in the optical properties of the biological sample and also a change in the composition of the coupling agent and, consequently, the physical properties of the coupling agent, such as its refractive index or its thermal conductivity. Coupling agents containing water and/or alcohol may extract materials such as salt and proteins from the tissue over a period of time. As a result, the properties of both the biological sample and the coupling agents may vary, and may contribute to changes in the signal over a period of time, i. e., drift.

The use of an appropriate coupling agent results in decreasing background variations in an optical measurement designed to determine the concentration of an analyte in a biological sample, including human tissue, such as the skin. The method of this invention results in decreasing drift in an optical measurement on a biological sample, such as, for example, the skin of a human forearm.

BRIEF DESCRIPTION OF THE DRAWINGS

FIG. 2A is a schematic diagram illustrating a branched optical fiber of an apparatus suitable for use in the method of this invention.

FIG. 2B is a schematic diagram illustrating optical fiber tips of an apparatus suitable for use in the method of this invention.

DETAILED DESCRIPTION

Figure 1:
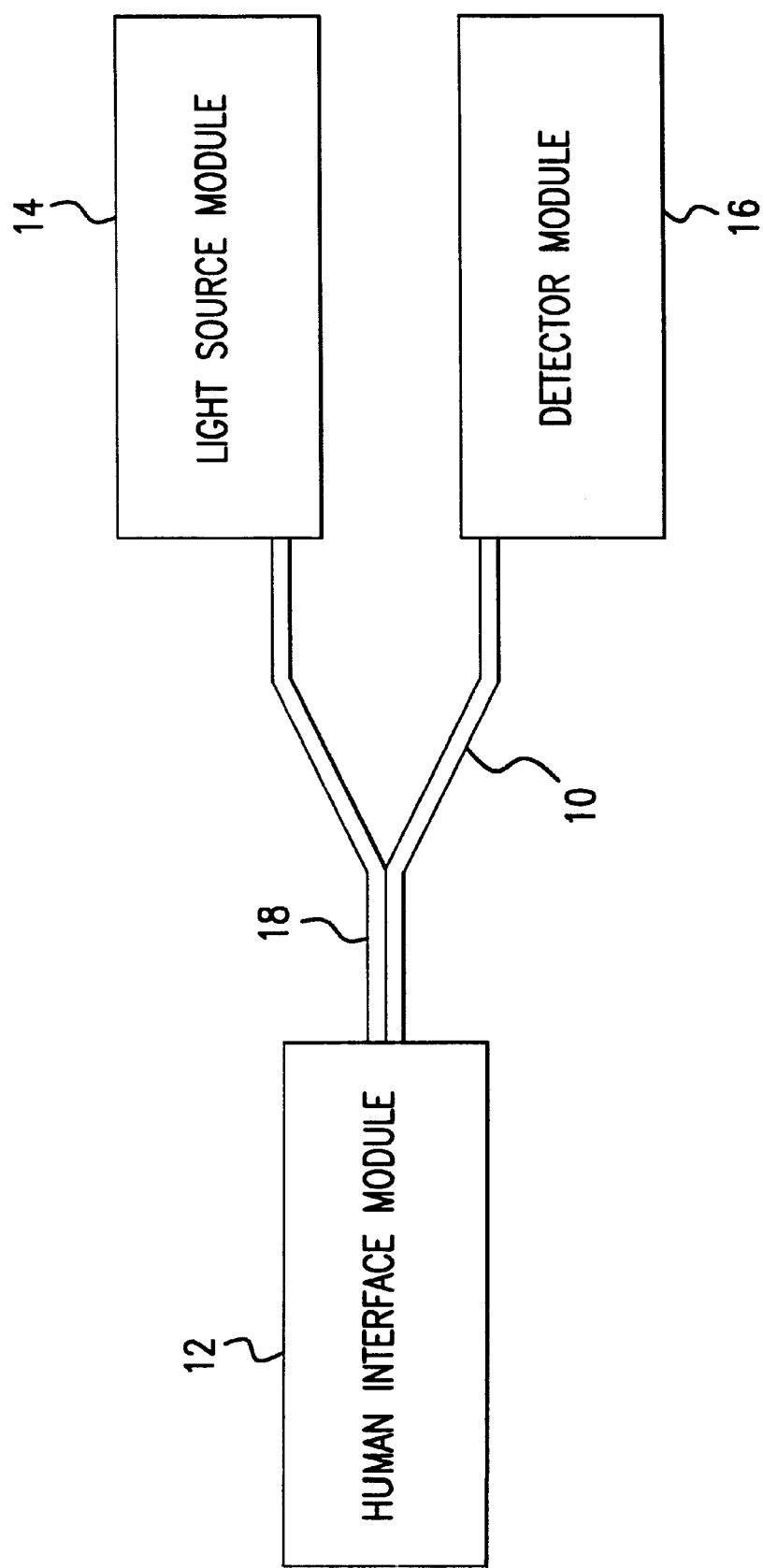
FIG. 1 is a block diagram illustrating an apparatus suitable for use in this invention.

As used herein, the expressions "optical probe" and "optical measuring instrument" are used interchangeably. The term "element" refers to a component of an optical measuring instrument. The expression "thermally controllable" refers to the ability of an element of an optical instrument to have its temperature controlled by external means. The term "interface" means a surface forming a common boundary between adjacent regions. The expression "biological sample" includes any tissue of a living animal, including humans. The tissue can be internal to the body of the animal or can be external to the body of the animal.

A calibration procedure is required for establishing a correlation between the non-invasive measurement of the optical properties of a biological sample and the concentration of an analyte in the same biological sample. One practical way to obtain calibration data involves inducing a change of the concentration of the analyte in the biological sample over a period of time by the injection of appropriate chemical compounds or, in the case of living animals, ingestion of food or drink. During this period of changing the concentrations of the analyte, non-invasive measurements of the optical properties are carried out either continuously or repetitively. Simultaneously, small samples are removed from the biological sample or the body part of the animal at certain time intervals during the same time period. The samples are subsequently analyzed by a standard method, i. e., a reference method, which is usually a chemical, biochemical, or electrochemical method, to determine the actual course of the changes in the concentration of the analyte during the time period. A correlation study is then carried out to establish a relationship (usually a mathematical relationship) between the change of the measured optical properties and the actual change of the concentration of the analyte. Such a relationship is thereafter used for the prediction of the concentration of the analyte from a non-invasive optical measurement.

A typical example of such calibration procedure involves blood glucose testing. Co-pending U.S. application Ser. No. 09/080,470 describes a non-invasive glucose sensor employing a temperature control. Co-pending U.S. application Ser. No. 09/098,049 describes methods for determining optical properties of tissue having more than one layer. Both of these applications teach techniques for carrying out optical measurements of a human tissue, or, more particularly, spatially resolved diffuse reflectance measurements of a human tissue. With such optical measurements, methods such as a Monte Carlo simulation can be used to deduce the optical properties or optical parameters, such as absorption coefficient ($\mu_a$) and scattering coefficient ($\mu_s$), for the tissue. Then, the optical properties of the tissue are correlated with the concentration of the analyte, i. e., glucose, in the tissue in a calibration procedure. When the correlation is established, the concentration of the analyte (glucose) in the tissue can be predicted by an optical measurement.

In a calibration procedure, one usually can induce a change in the glucose concentration in the blood of a subject in a number of ways. The most common and the easiest way is to allow the subject to ingest food or drink containing a large amount of carbohydrates or sugars in a meal tolerance test procedure. Alternatively, the drink can be a solution having high glucose (or dextrose) concentration in an oral glucose tolerance test procedure. Both the meal tolerance test and the oral glucose tolerance test will cause a substantial increase in the test subject's blood glucose level in about 30 minutes to 60 minutes. After a peak level of glucose concentration is reached, the glucose concentration starts to decrease, and returns to the level prior to the food or drink ingestion in about two to four hours. Alternatively, a glucose solution can be injected into a vein of the subject, which will induce an almost instantaneous increase of the blood glucose level of the subject. Similarly, a glucose regulating agent, such as insulin, can be injected into a vein of the subject, which will induce an almost instantaneous decrease of the blood glucose level of the subject.

At different points in time during the course of the changing of the glucose level, optical measurements can be performed upon a tissue of the subject's body part to obtain the optical properties of the tissue. Simultaneously, a reference method can be used to determine the actual blood glucose concentration of the subject at the same points in time that the optical measurements are performed. The commonly used reference method includes withdrawing a blood sample from the subject by means of venous puncturing or a finger stick and analyzing the blood sample by means of a chemical or an electrochemical method to determine the concentration of the glucose in the blood sample.

Co-pending U.S. application Ser. No. 09/080,470, incorporated herein by reference, describes a glucose sensor employing a temperature control for non-invasive measurements. One purpose of controlling the temperature is to minimize the effect of physiological variables. Appropriate selection of the temperature value results in improvement in the background signal drift as well. Nevertheless, it has been found that, even with the temperature-controlling device employed with this sensor, it is desirable to further reduce drift significantly.

The method of U.S. application Ser. No. 09/080,470, like most methods described in the art for non-invasive measurement of analytes in human tissue, involves measurement of transmitted or diffusely reflected light from tissue and requires the step of contacting an optical probe to the surface of the tissue of a human body part. Mechanical and thermal interactions between the optical probe and the tissue will induce the re-distribution of heat in the tissue and the deformation of the structure of the tissue, particularly the stratum corneum layer in the case of the skin. These changes, in turn, will promote a series of physiological responses, including capillary vasomotion, vein dilation, and sweating. As a result, the optical properties of the tissue around the area contacted by the probe will be changed. The period of time required to reach a relatively steady state for such changes can vary from a few seconds to several minutes and is highly dependent on such factors as the temperature of the probe, pressure of the probe against the tissue, area of contact of the probe, etc., as well as the physical and physiological conditions of the subject being tested, such as body temperature, thickness of the epidermis, and muscle and fat content. Unfortunately, such complicated relationships make the changes in the end result, i.e., the measured reflected light signal and hence the calculated optical properties of the tissue, highly uncontrollable and unpredictable. Change in the measured optical signal as a function of time, independent of change in concentration of the analyte of interest in the tissue, is usually called background signal drift.

Background signal drift is often characterized as the change of signal over time, with the magnitude and direction of change being unpredictable. This unpredictability of change of signal is more likely to create random errors rather than bias errors for the determination of optical properties. Therefore, it is unlikely that background signal drift can be corrected through calibration, or by correcting the optical aberration, such as mismatches of the refractive indexes in the region of the interface of the tissue and the optical device.

Background signal drift appears to be most severe shortly after the optical probe contacts the tissue (typically in the first five minutes). During this period, the signal amplitude may vary by 5% to 20% or even higher, even in the absence of any traceable changes in concentration of all analytes. Additional background signal drift may occur over an extended period of time, i. e., background signal drift could range anywhere from 0% to 20% or even more in, for example, 30 minutes. These changes may be much greater than the changes in a specific signal, which changes are usually less than 5% due to changes in the concentration of analyte. Background signal drift is probably the most challenging problem encountered in most non-invasive methods. For example, during the oral glucose tolerance test, to avoid errors resulting from the re-contacting of the optical probe to the skin, the optical device is usually applied continuously to the skin for approximately two hours. However, during this period, drift is usually so severe that so far no one has been able to claim success in tracking glucose over the duration of an oral glucose tolerance test.

FIG. 1 is a schematic diagram of an apparatus 10 suitable for use in the present invention. This apparatus can provide spatially resolved diffuse reflectance measurements, i. e. R(r), from the skin of a human body part, e. g., a forearm. The diffuse reflectance measurements, R, at a plurality of distances, $r_1, r_2, \ldots, r_n$, allow the determination of the optical properties, such as absorption coefficient ($\mu_a$) and scattering coefficient ($\mu_s$), for the skin at a depth of less than three millimeters from the surface of the skin. The details of the apparatus and the method for the determination of optical properties can be found in co-pending U.S. application Ser. No. 09/080,470. The apparatus 10 comprises three modules: a human interface module 12; a light source module 14; and a detector module 16. As shown in FIG. 1, the human interface module 12 is connected to the light source module 14 and the detector module 16 via a bifurcated optical fiber probe 18.

FIG. 2A is an illustration of the bifurcated optical fiber probe 18. The bifurcated optical fiber probe is constructed from Anhydrous G Low OH VIS-NIR optical fibers. As shown in FIG. 2B, the fiber probe has three distinct termination points or "tips". During operation, the source tip 20 is contained within the light source module 14, the detector tip 22 is contained within the detector module 16, and the common tip 24 is contained within the human interface module 12. A single optical fiber 26 transmits light from the source tip 20 to the common tip 24. Six optical fibers (28, 30, 32, 34, 36, and 38) transmit light from the common tip 24 to the detector tip 22.

Light source module 14 includes a source of modulated light (not shown), such as a Gilway L1041 lamp modulated with a Stanford Research Optical Chopper. A prism, a dichroic beam splitter, or the like may be used to direct a portion of the beam emanating from the light source to a reference detector, such as a Hammamatsu S-2386-44K 6C Silicon Detector, in order to normalize the measurements for fluctuations in source intensity. The rest of the light emanating from the light source is focused onto the end of the source tip by means of at least one focusing lens. Additional optical elements, such as attenuators, optical filters, and irises may be inserted between the light source and the source tip. The source tip is preferably held in an adapter having provisions for adjusting the location of the source tip with respect to the beam emanating from the light source.

The common tip 24 is installed in the human interface module, which is placed against a body part during use. As shown in FIG. 2B, the common tip comprises the source fiber 26 and six additional fibers (28, 30, 32, 34, 36, and 38) that collect the light that is scattered by the tissue sample.

Fibers 28, 30, 32, 34, 36, and 38 are located at increasing distances from the source fiber 26 within the common tip. The relative distances between the center of the source fiber 26 and the centers of collection fibers 28, 30, 32, 34, 36, and 38 of the common tip can be seen in FIG. 2B. In a preferred embodiment, all of the collection fibers are located at separation distances that are less than 4 mm and, preferably, less than 2 mm away from the source fiber 26. As will be more thoroughly described below, these distances provide very good precision and accuracy.

The six collection fibers 28, 30, 32, 34, 36, and 38 are arranged in a circle within the detector tip 22 as shown in FIG. 2B with sufficient spacing to allow a shutter to interrogate each fiber individually. The detector module receives the detector tip and holds it adjacent to a rotating shutter (not shown) that allows detection of the light emitted from one fiber at a time. The shutter has a detent or other means to lock it in the six fiber positions. The light from the fiber of interest is focused on a detector by a pair of 25 mm diameter, 60 mm focal length Achromatic lenses. The detector is a Hammamatsu S-2386-44K 6C Silicon Detector. The detector module also comprises appropriate electronic signal processing instrumentation such as large dynamic range amplifiers and lock-in amplifiers. Alternatively, the outputs of the six fibers can be directed to six detectors for parallel signal processing.

Figure 3:
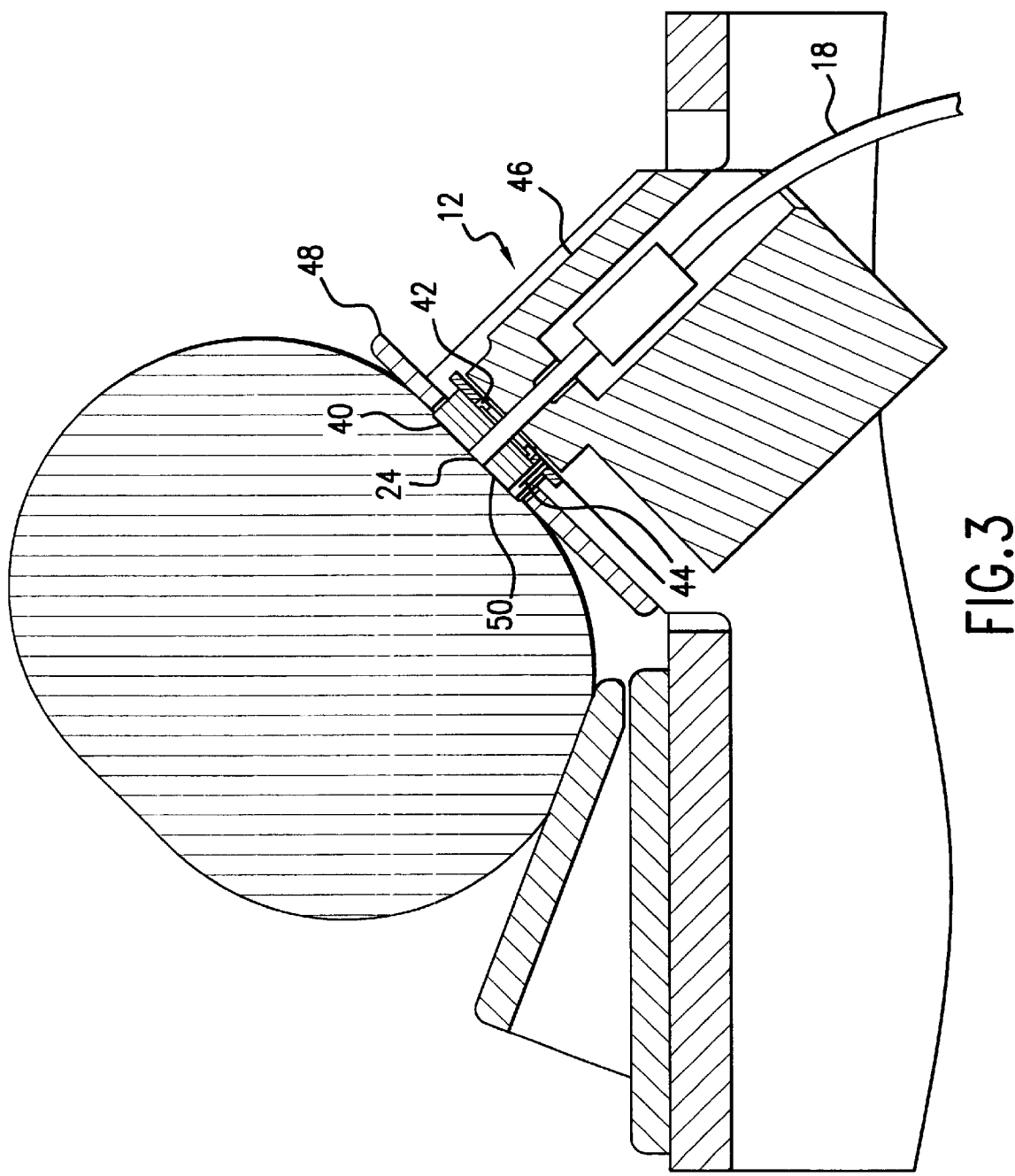
FIG. 3 is a schematic diagram illustrating a part of the human interface module of an apparatus suitable for use in the method of this invention.

FIG. 3 illustrates the human interface module 12, which comprises an aluminum disk 40, a thermoelectric cooling element 42, a thermocouple 44, a heat sink 46, the common tip 24, and an interface adapter 48. The aluminum disk contains an aperture 50, which receives the common tip 24 of the bifurcated optical fiber probe 18 and holds the common tip 24 against the body part. The temperature of the aluminum disk 40 (and of the tissue adjacent the disk 40) is controlled by a thermoelectric cooling element 42, such as a Marlow Industries model number SP1507-01AC. The thermoelectric cooling element 42 is powered by a temperature controller/power supply, such as a Marlow Industries model number SE5000-02. The heat sink 46 is provided on the back of the thermoelectric cooling element 42 to enhance heat transfer. The interface adapter 48 is shaped to conform to a body part and may, for example, be cylindrical, flat, spheroidal or any other shape. The interface adapter 48 improves the efficiency of the optical and thermal coupling of the aluminum disk 40 and the common tip 24 to a body part.

Figure 4:
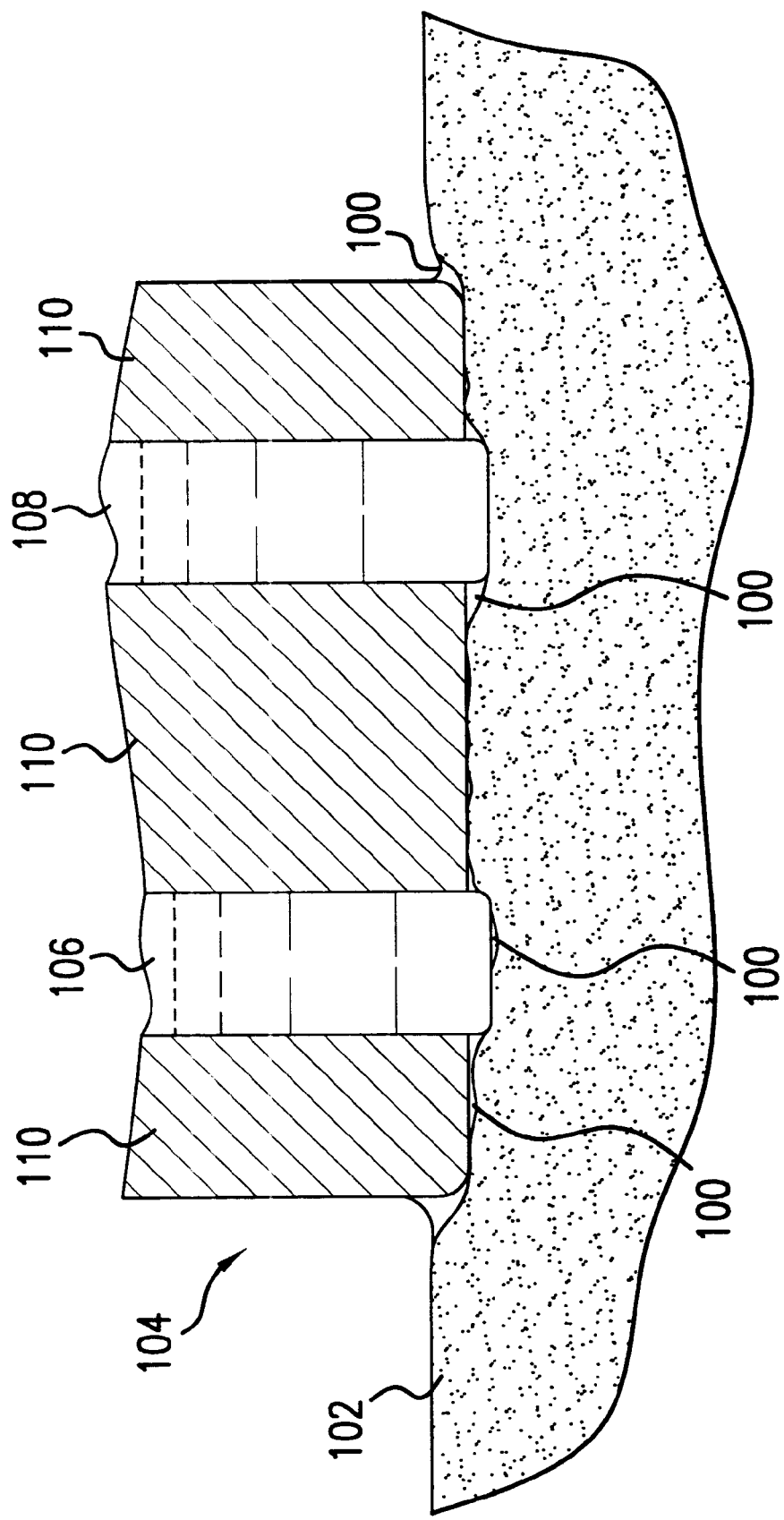
FIG. 4 is a schematic diagram illustrating the interfaces between the optical probe, with a heating element, and the coupling agent and the coupling agent and the skin.

Referring to FIG. 4, the use of a coupling agent 100 is required to achieve mechanical compliance between the skin 102 and the optical instrument 104. Thus, the usually uneven skin surface is brought into thermal and optical contact with optical measuring elements 106 and 108 of the optical instrument 104 and the thermal control element 110 of the optical instrument 104, thereby allowing better temperature control and heat transfer. Optical properties of tissues are affected by temperature. Efficient heat transfer between the skin 102 and the thermal control element 110 leads to better control of tissue temperature and hence a more stable optical signal. The thermal control element 110 corresponds to the aluminum disk 40 of FIG. 3. The optical measuring elements 106 and 108 correspond to the optical fibers in the common tip 24 of FIG. 3. The optical measuring element 106 is a light introduction fiber; the optical measuring element 108 is a light collection fiber.

A coupling agent suitable for this invention must have several properties to enable it to help decrease measurement variation, especially drift. One of the most important properties is sufficiently high optical stability that the optical properties of the coupling agent do not change even during prolonged experiments, such as meal tolerance tests and oral glucose tolerance tests. The optical properties of the coupling agent should also remain stable during storage. Thus, hygroscopic agents, such as glycerol, are not suitable as coupling agents for this invention because they absorb water from both the skin and the atmosphere, which causes their physical properties to change over time.

Secondly, the coupling agent should have sufficiently high thermal conductivity to allow fast, efficient heat transfer between the optical probe and the tissue. The thermal conductivity of the coupling agent should be at least four times that of air, i. e., greater than 1 miliwatt/cm/° C.

Third, the coupling agent should have sufficiently high viscosity to prevent it from migrating from the measurement area. Yet, it should also have sufficiently low viscosity to allow sufficient contact between the optical probe and the skin and to permeate into any small pockets between the probe and the skin that would otherwise be filled with the air. The preferred viscosity of the coupling agent ranges from about 10 centipoises to about 100,000 centipoises.

Fourth, the coupling agent should be inert. Material from the coupling agent should not diffuse into the biological sample and material from the biological sample should not diffuse into the coupling agent. Thus, coupling agents containing a high concentration of water or alcohol are not suitable for this invention. Low molecular weight compounds, such as water or alcohol, can diffuse into the biological sample, thereby causing a change in the optical properties of the sample and also a change in the composition of the coupling agent and, consequently, the physical properties of the coupling agent, such as its refractive index or its thermal conductivity. Coupling agents containing water and/or alcohol may extract materials such as salt and proteins from the biological sample over a period of time. As a result, the properties of both the sample and the coupling agents may vary, and may contribute to changes in the signal over time, i. e., drift.

It is preferred that the coupling agent be thermally stable at temperatures ranging from 10° C. to 45° C. It is also preferred that the coupling agent be inert to oxygen at temperatures ranging from 10° C. to 45° C.

Coupling agents that have been found suitable for use in the method of this invention include silicone oil and mineral oil. Silicone oil includes, but is not limited to, any fluidic organosilicon oxide polymer having the repeating structural unit —$R_2Si$—O—, where R represents a monovalent organic radical, such as methyl or phenyl. As used herein, mineral oil is a mixture of liquid hydrocarbons. A commercially available silicone oil is poly(dimethylsiloxane), which can have viscosity ranging from 5 to 100,000 centipoises, depending on the molecular weight of the polymer. A typical silicone oil that is suitable for use in this invention is commercially available from Aldrich Chemical Company, Catalog No.14,615-3. This silicone oil has a viscosity of about 48 centipoises, a thermal conductivity of about 1.5 milliwatt/cm/° C., an index of refraction of about 1.404, and a density of about 0.963 kg/L. Mineral oil is also known by the names of paraffin oil and liquid petrolatum, which are derived almost exclusively from petroleum. According its density, mineral oil can be categorized as a light oil or as a heavy oil. A typical mineral oil that is suitable for use in this invention is commercially available from Aldrich Chemical Company, Catalog No. 33-076-0. This mineral oil has a viscosity of about 35 centipoises, a thermal conductivity of about 1.3 milliwatt/cm/° C., an index of refraction of about 1.476, and a density of about 0.862 kg/L.

Coupling agents suitable for this invention also include other kinds of fluids that have the thermal conductivity, viscosity, and refractive index within the ranges specified herein. For example, synthetic liquid materials such as polyethylene glycols and other oils from plants, animals, or other natural resources may also be suitable candidates for coupling agents. Interference resulting from any interaction of the coupling agent with biological tissue is defined according to its practical effect on optical signals in a specific application. For some measurements, particularly those carried out within a short period of time, the exchange of components between the tissue and the coupling agent may be of little or no concern. Therefore, one of ordinary skill in the art may still use some water-based or alcohol-based liquids, such as aqueous gels or mixtures of glycerol and water, as coupling agents to control optical signal drift.

U.S. Pat. No. 5,655,530 describes the use of hydrophobic, refractive index matching optical coupling fluids. One class of such compounds includes chlorinated-fluorocarbons. The coupling agent useful in the present invention need not be a hydrophobic agent nor have its refractive index match that of the skin. As will be described later, coupling agents having refractive index values significantly higher than that of the skin were found to decrease drift of the observed signal effectively. Optically clear coupling agents having sufficiently high viscosity and sufficiently high thermal conductivity are required. Index matching is not required, because specular reflection does not substantially contribute to the measured reflected signal at a distance (i. e., r) from the light introduction site. Further, chlorinated fluorocarbons may have an adverse effect on the skin by interacting with lipid components in the stratum corneum.

U.S. Pat. No. 5,823,951 describes the use of hydrophilic, refractive index matching fluids to decrease the specular reflection component of diffusely scattered light. Liquids containing chloro-fluoro hydrocarbons, alcohols, and surfactants are representative examples of refractive index matching fluids for serving as the coupling agent between the probe and the skin. As will be described in the examples, the use of hydrophilic coupling agents such as glycerol or a mixture of glycerol and water does not reduce drift of the observed signal. Moreover, the use of alcohols, such as isopropyl alcohol, is not desirable, as alcohol molecules will diffuse into the stratum corneum, changing it optical properties over time, and potentially resulting in drift. Alcohol and surfactants also affect the mechanical properties of the stratum corneum.

The use of refractive index matching fluid decreases the variability due to Fresnel losses at the probe/skin interface. The technique of Messerschmidt does not apply for the case of collection optical probe touching the surface of the tissue at a separation distance from the light illumination point. Further, Messerschmidt did not disclose the temperature at which this refractive index matching fluid is used. The refractive index of fluids is strongly dependent on temperature; the refractive index generally decreases as the temperature increases. Thus, if the refractive index of an optical coupling fluid at 20° C. matches the refractive index of the skin, it will decrease as the optical probe is brought in contact with the skin and reaches body temperature (34° C. to 37° C.). Under this condition, refractive index mismatch will occur again, leading to Fresnel losses, and hence giving rise to the variability in the measurement as temperature equilibration is approached. It is preferable to select an inert, non-diffusing fluid having a refractive index, measured at 20° C., higher than that of the skin (about 1.38) and close to that of the optical fibers that illuminate the skin and detect the re-emitted light.

Unlike U.S. Pat. Nos. 5,655,530 and 5,823,951, U.S. Pat. No. 4,975,581 discloses the use of mathematical manipulation of the data to mask the effect of drift of the signal.

In the method described in this invention, a thermally controllable optical probe for spatially resolved diffuse reflectance measurement is used to collect optical signal from the skin. As the thermally controllable optical probe is brought into contact with the skin and a coupling agent having a higher refractive index than that of the stratum corneum, the refractive index of the coupling agent decreases and the refractive index mismatch between the skin and the coupling agent decreases. In all cases, the coupling agent should be selected to have a refractive index higher than that of the skin over the temperature range of the measurement.

Refractive indices of liquid mixtures will exhibit more complex dependence on temperature than will the refractive index of a single liquid. The optical signal from a liquid mixture will exhibit more complex behavior as temperature and time of contact change than will the optical signal from a single liquid. Thus, in a temperature controlled measurement of concentration of analyte in a layer of the skin, matching the refractive index of the coupling agent to that of the skin is not important and may even lead to inaccurate measurement at different temperatures. However, because of the dependence of the refractive index on temperature, and the dependence of the tissue scattering on temperature, it is important to establish appropriate thermal contact between the temperature controllable optical probe and the skin in order to achieve reproducible thermal equilibrium within the dermis layer of the skin. Thermal contact between the optical probe and the skin, without air gaps between them and with inert, highly thermally conductive fluids (or gels), will cause the temperature in the volume of the skin in which the concentration of analyte is being measured to closely track the temperature of the optical probe and will lead to improvement in signal response to a controlling temperature, i. e., drift will decrease during the early phase of the measurement. Thus, the decrease in drift in the measurement is achieved by the use of a thermally conductive coupling agent having refractive index higher than that of the skin at all measurement temperatures and by the control of the temperature of the skin at the measurement site.

Thus, the refractive index of the coupling agent does not need to match the refractive index of the skin. As in most other applications, as shown in FIG. 4, the optical measuring elements 106 and 108 have refractive indices equal to or greater than 1.5, and the refractive index of the skin 102 is about 1.38. When the coupling agent 100 (e. g., silicone oil, which has refractive index of 1.404) is applied, there are still significant mismatches among the optical fiber, coupling agent, and skin according to the method employing refractive index values at the room temperature. However, because the distance between the light introduction fiber 106 and the light collection fiber 108 is on the order of 0.4 mm or greater, the effect of specular reflection in the measurement is insignificant.

The following, non-limiting examples will further illustrate this invention.

EXAMPLES

Example 1

FIGS. 1, 2, and 3 illustrate an apparatus for the measurement of optical properties of samples that scatter light, and hence the concentration of different analytes at various depths of the samples. Further details of this apparatus are provided in co-pending U.S. application Ser. No. 09/080, 470, filed May 18, 1998, assigned to the assignee of this application, incorporated herein by reference. The apparatus can be used to measure reflectance of light re-emitted from the skin of human subjects.

As shown in FIG. 1, the apparatus 10 comprises a light source module 14, a human interface module 12, a signal detector module 16 and a branched optical fiber bundle 18 that conducts light signals among these three modules.

Monochromatic light is generated from the light source module 14 alternatively at six wavelengths, i.e., 590 nm, 650 nm, 750 nm, 800 nm, 900 nm, and 950 nm. Different wavelength sets can be obtained by replacing one or more of the bandpass filters of the existing set. This light is transmitted to the human interface module 12 through a source fiber 26 in the branched optical fiber bundle 18 (FIGS. 2A and 2B). The source fiber 26 receives light from one end housed in a source tip 20 in the light source module 14, and emits the light into the skin of a subject's forearm from its other end, which directly touches the skin at a point designated as the light introduction site, housed in the common tip 24 in the human interface module 12. Also in contact with the skin from the common tip 24 are six other fibers 28, 30, 32, 34, 36 and 38, which are six independent light collection elements. Each of these fibers collects light re-emitted from the skin at the point where it touches the skin, i. e., a light detection site. The human interface module 12, with its main components illustrated in FIG. 3, engages the common tip 24 to the skin. The human interface module also provides temperature and pressure control mechanisms (numerals 40, 44 and 46 in FIG. 3) for the area where the common tip 24 contacts the skin. In addition, the human interface module has a comfortable armrest (numeral 48 in FIG. 3) for the testing forearm. The measuring step is confined to a depth in the tissue wherein the temperature is controlled. This depth is preferably less than three millimeters, more preferably less than two millimeters, from the surface of the skin.

Both the source fiber and detection fibers have diameters of 400 $\mu$m. The distance from any one detection fiber 28, 30, 32, 34, 36 or 38 to the source fiber 26 at the end of the common tip 24 defines the distance, measured across the surface of the skin, between the corresponding light collection site and the light introduction site. These distances are listed in TABLE 1.

TABLE 1

| Collection fiber | 28 | 30 | 32 | 34 | 36 | 38 |
|---|---|---|---|---|---|---|
| Nominal distance from light introduction fiber, mm | 0.44 | 0.78 | 0.92 | 1.22 | 1.40 | 1.84*<br>1.82** |

*See FIGS. 5B, 5D, 7B, and 7D.
**See FIGS. 6B, 6D, 6F, and 6H.

The six light collection fibers receive the light re-emitted from the skin at the common tip 24 and transmit the light to the detector tip 22 housed in the detector module 16. The ends of each of these fibers at the detector tip 22 are in the focal plane of a lens (not shown) for a silicon detector (not shown). However, the light signal from that fiber is detected only when the shutter (not shown) between a particular fiber end and the detector is opened.

Therefore, the sampling distance r (as illustrated in FIG. 4) is determined by selecting a particular light collection fiber and then allowing the detector associated with that collection fiber to measure the intensity of the re-emitted light collected by this fiber. This determination is achieved by the use of a programmable shutter that selects the particular one of the six fibers that collects light re-emitted from the skin. The movement of the shutter is effected by rotating the shutter a programmed number of steps or to a pre-selected detent on its mount. All collection fibers other than collection fiber 28 are at relatively great distances from the light introduction fiber 26, and therefore are not significantly affected by the specular reflectance.

Example 2

This example demonstrates the effect of different coupling agents on the reduction of drift in a spatially resolved diffuse reflectance measurement under the condition of constant temperature.

a. Effect of silicone oil

In the first measurement, a healthy male subject was tested with the apparatus described in Example 1. No coupling agent was used. A few hours later, in the second measurement, an identical experiment was conducted on the same subject, with the only exception that a coupling agent was applied. The measurement site was on the left forearm in both measurements.

The coupling agent used was silicone oil (from Aldrich Chemical Company, Cat. No. 14,615-3). The coupling agent had a refractive index of 1.404 and density of 0.963 kg/L.

The temperature was set at 34° C. throughout the both measurements. Before the second measurement, one drop of the silicone oil was spread over the testing site on the subject's left forearm, and another drop of the silicone oil was spread over the tip 24 of the optical fiber and the aluminum disk 40. When the optical probe was brought in contact with the skin, the oil formed a very thin layer between them, due to the low viscosity of the silicone oil.

Figure 5A:
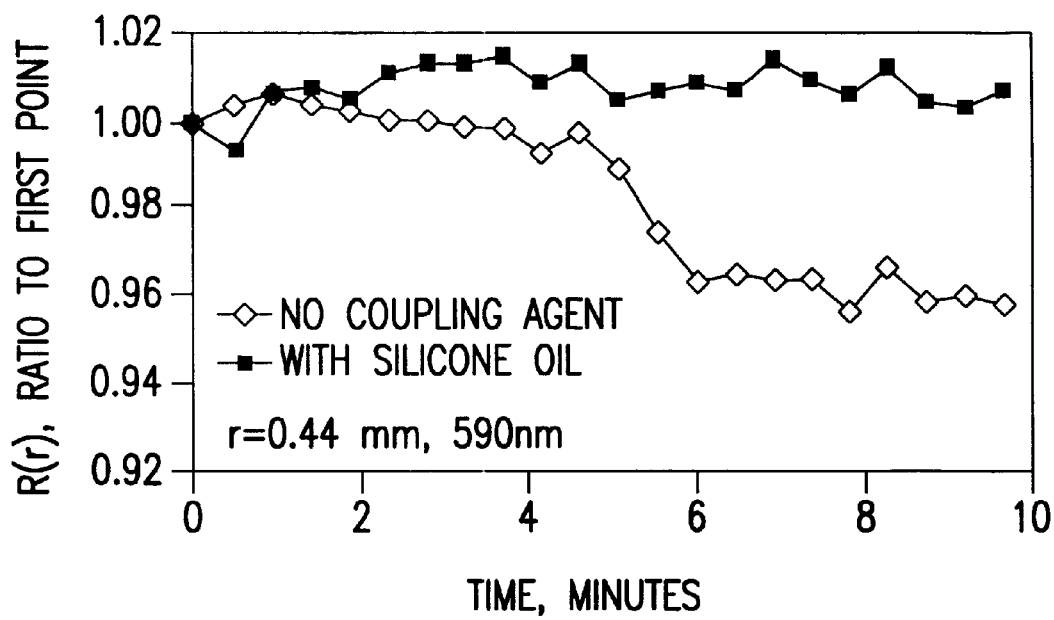
FIGS. 5A, 5B, 5C, and 5D are graphs illustrating change in diffuse reflectance as a function of time at constant temperature. The graphs show the effect of silicone oil as a coupling agent.
Figure 5B:
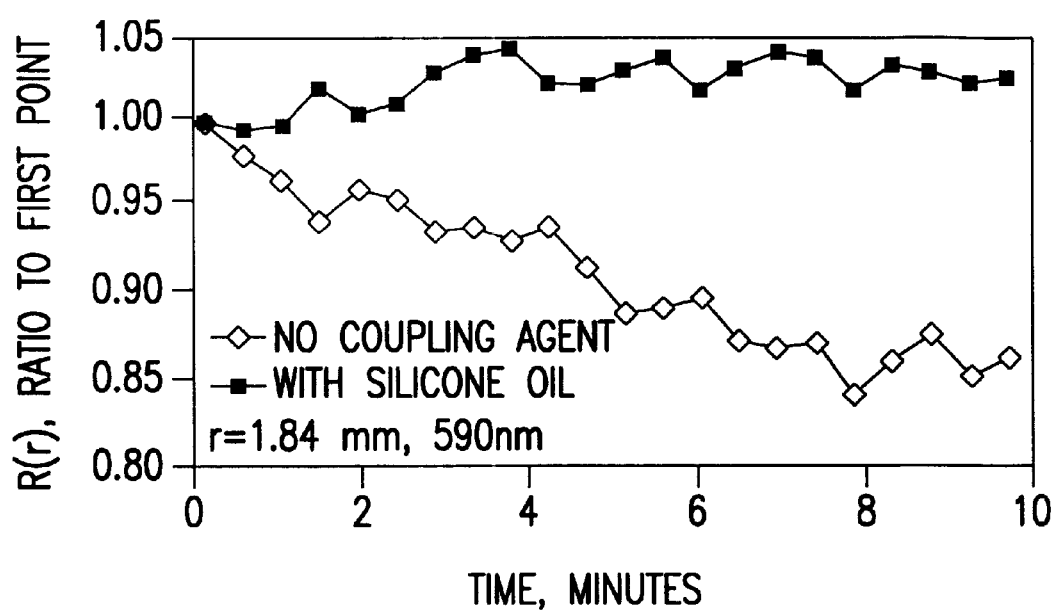
Figure 5C:
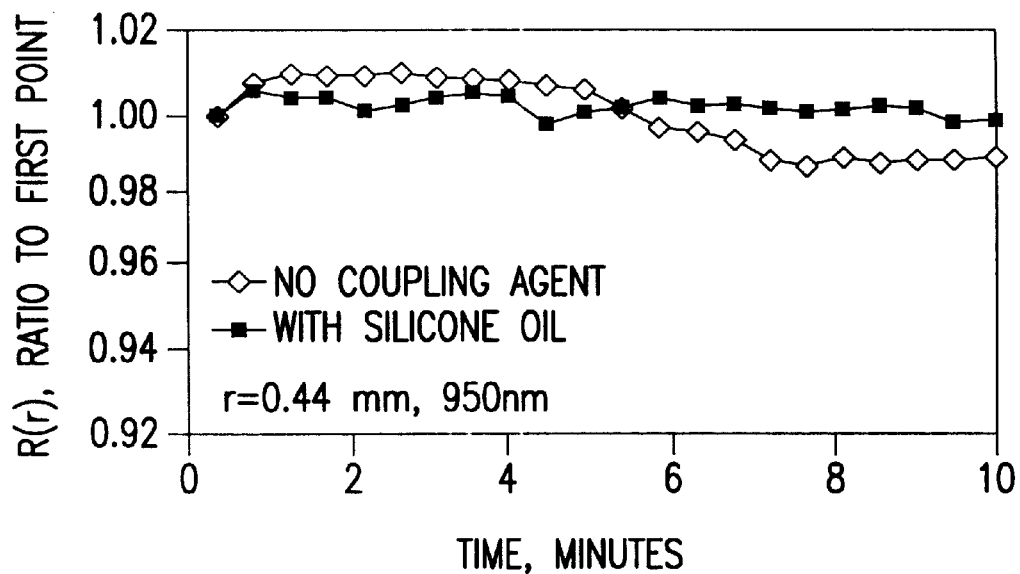
Figure 5D:
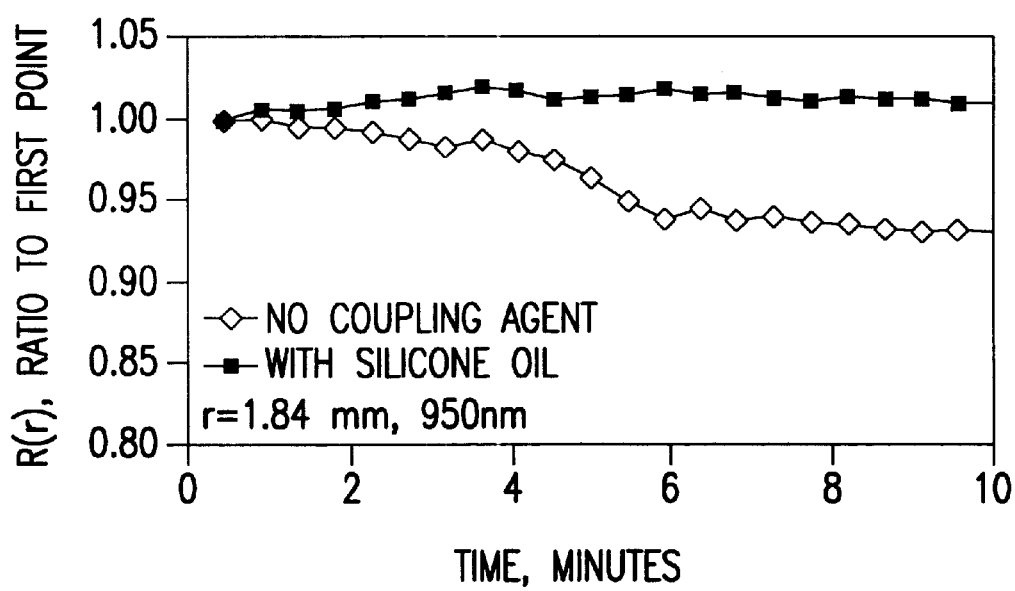
Figure 5E:
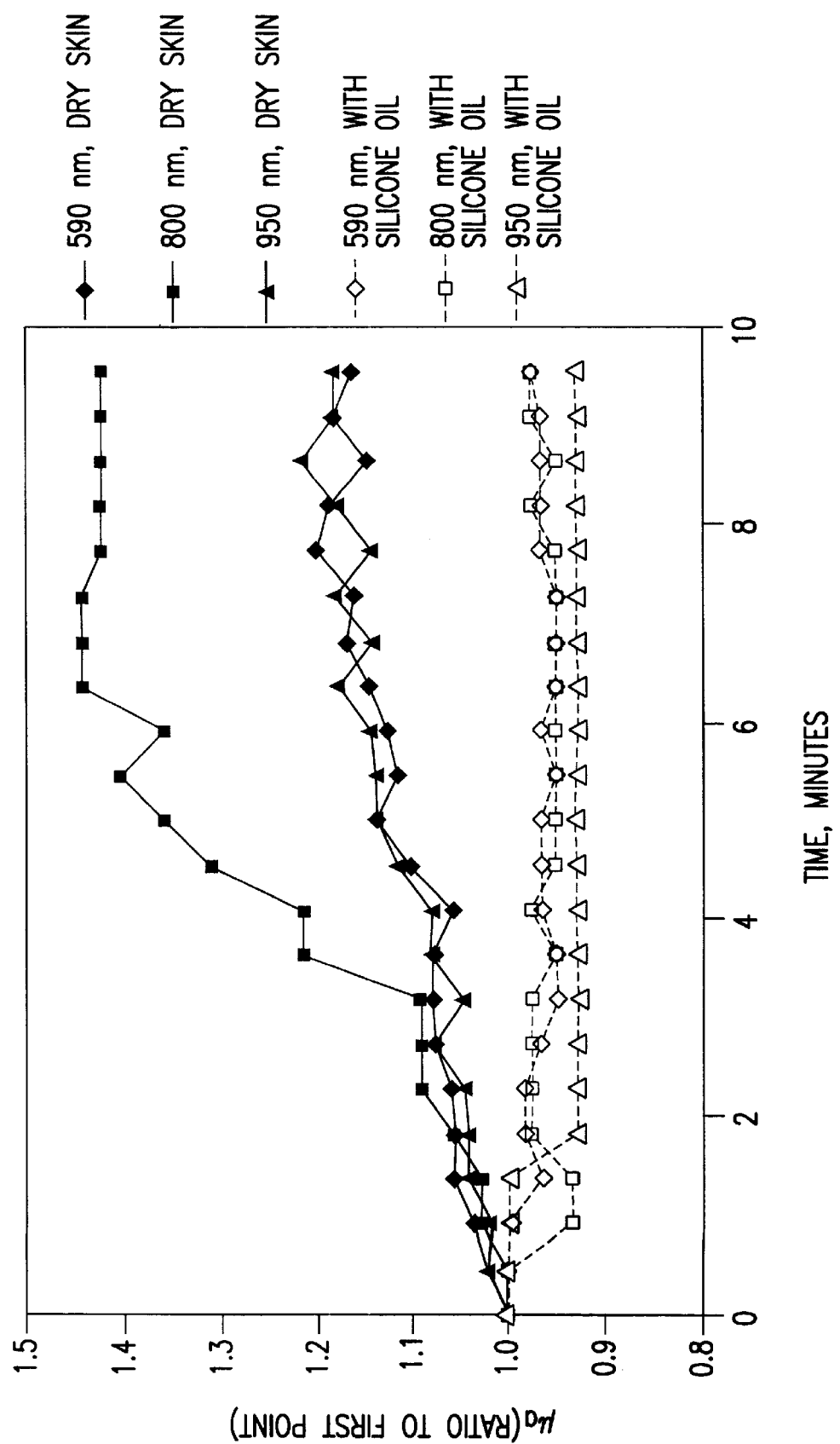
FIG. 5E is a graph illustrating change of absorption coefficient as a function of time at constant temperature. The graph shows the effect of silicone oil as a coupling agent.
Figure 6A:
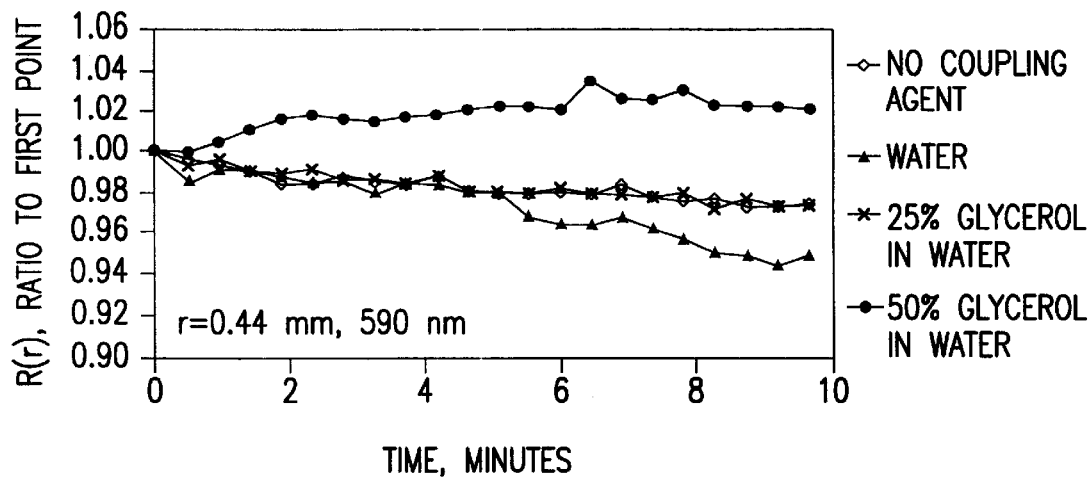
FIGS. 6A, 6B, 6C, and 6D are graphs illustrating change in diffuse reflectance as a function of time at constant temperature. The graphs show the effect of materials other than oil as coupling agents.
Figure 6B:
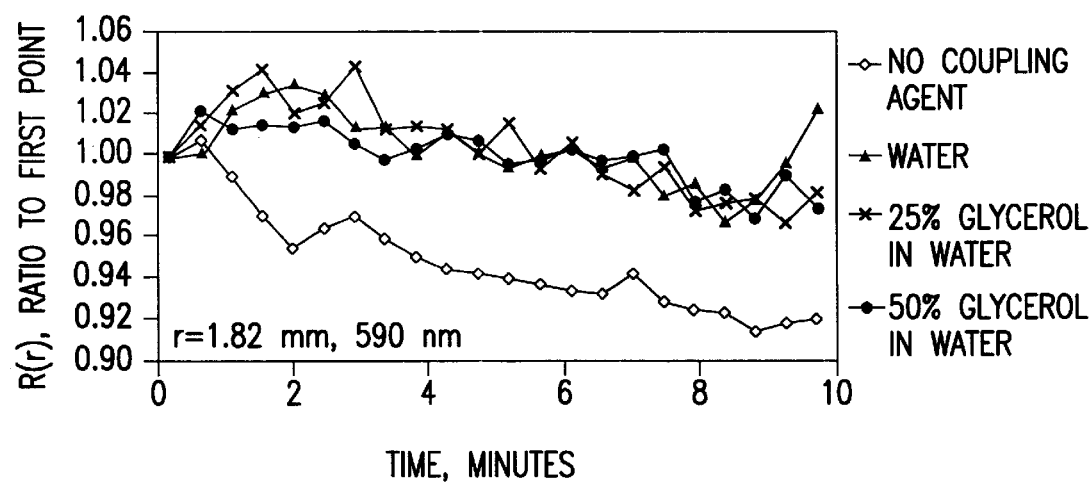
Figure 6C:
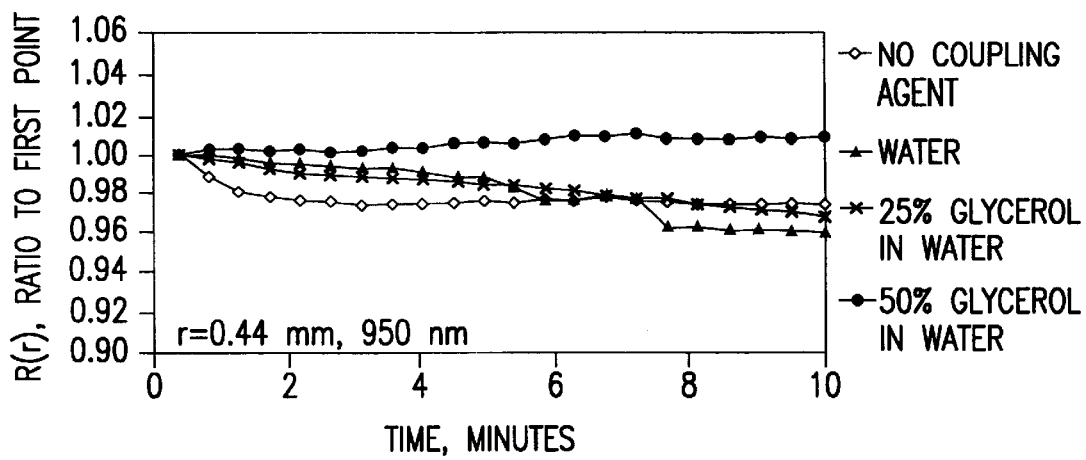
Figure 6D:
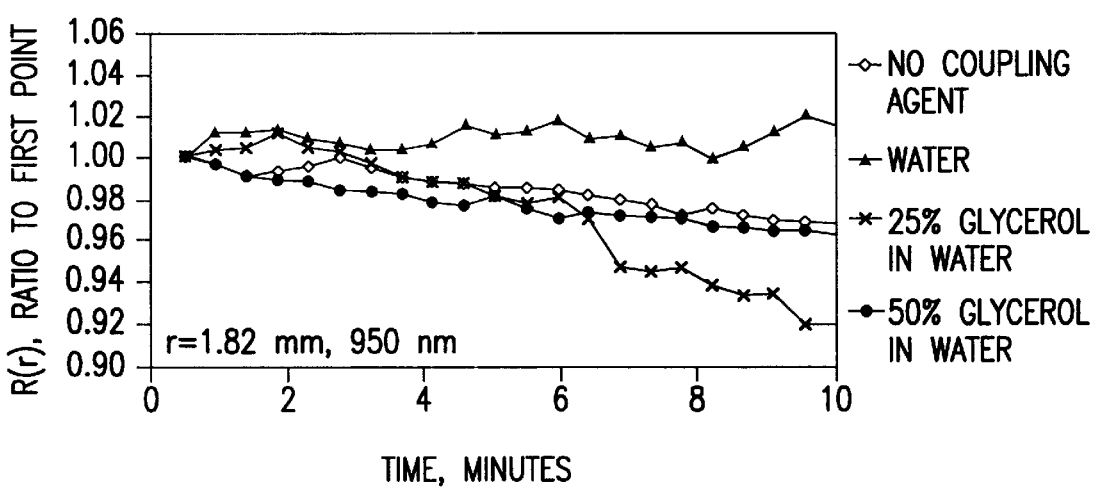
Figure 6E:
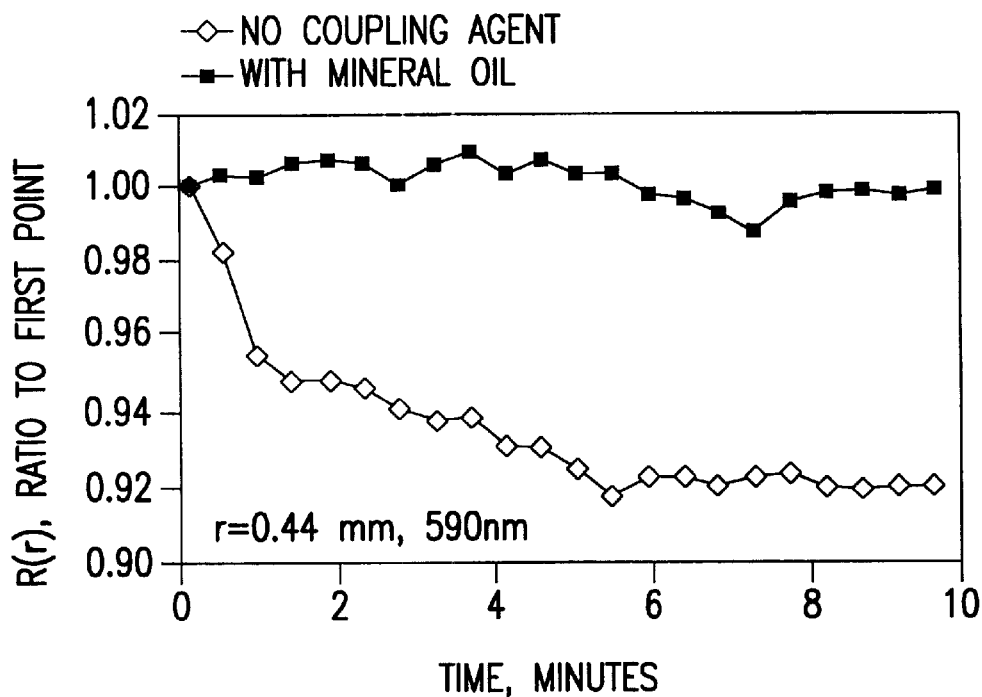
FIGS. 6E, 6F, 6G, and 6H are graphs illustrating change in diffuse reflectance as a function of time at constant temperature. The graphs show the effect of mineral oil as a coupling agent.
Figure 6F:
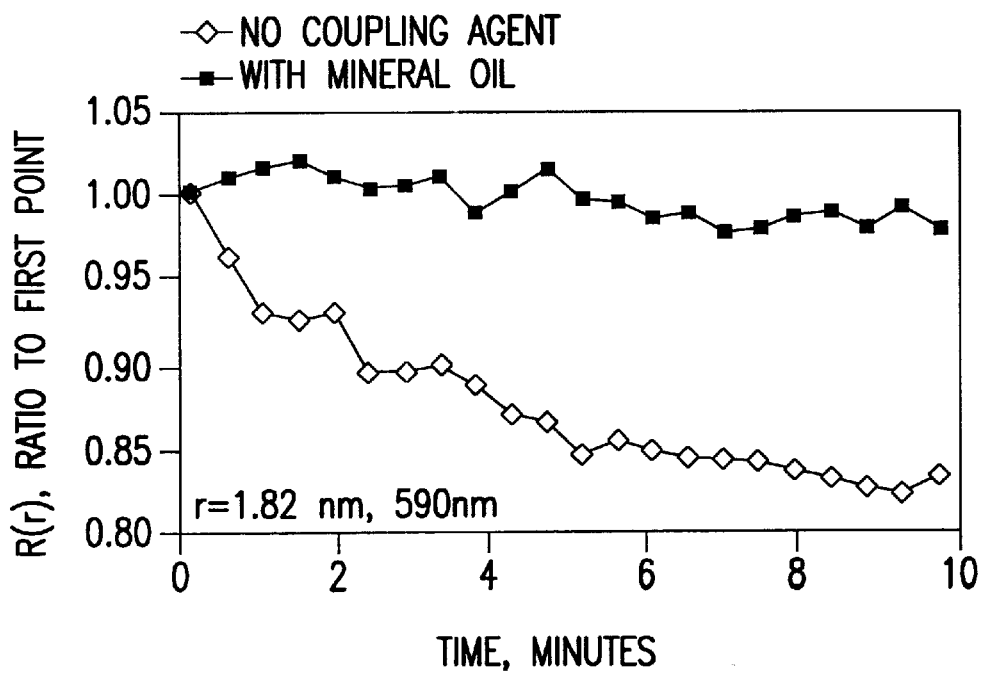
Figure 6G:
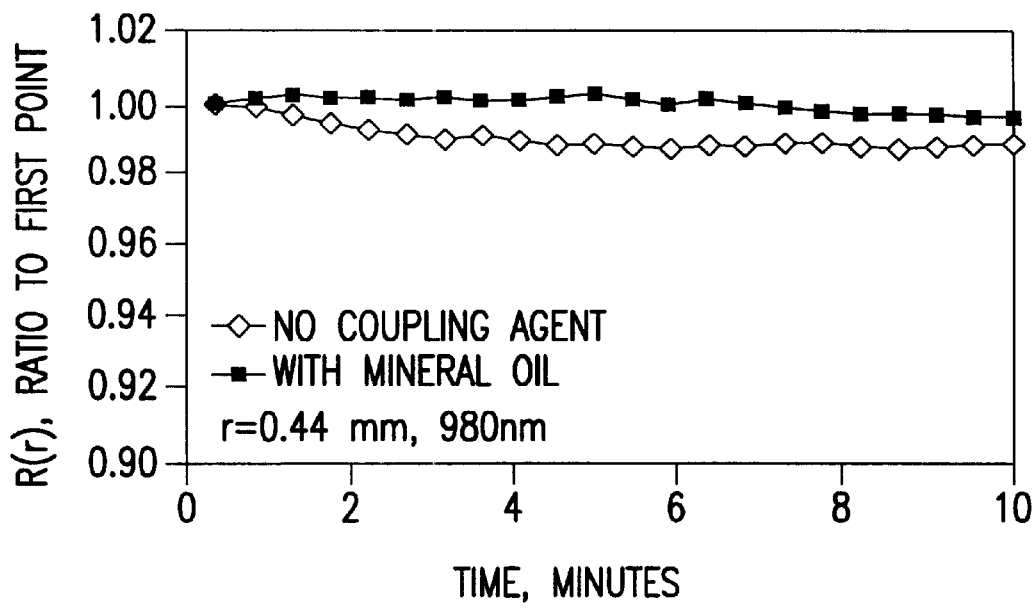
Figure 6H:
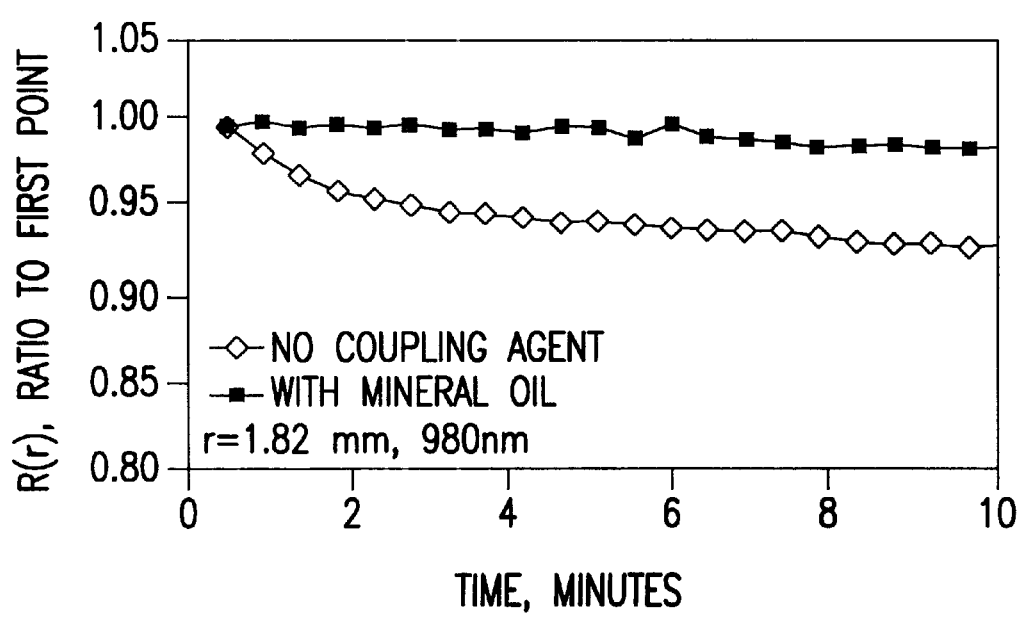
Figure 7A:
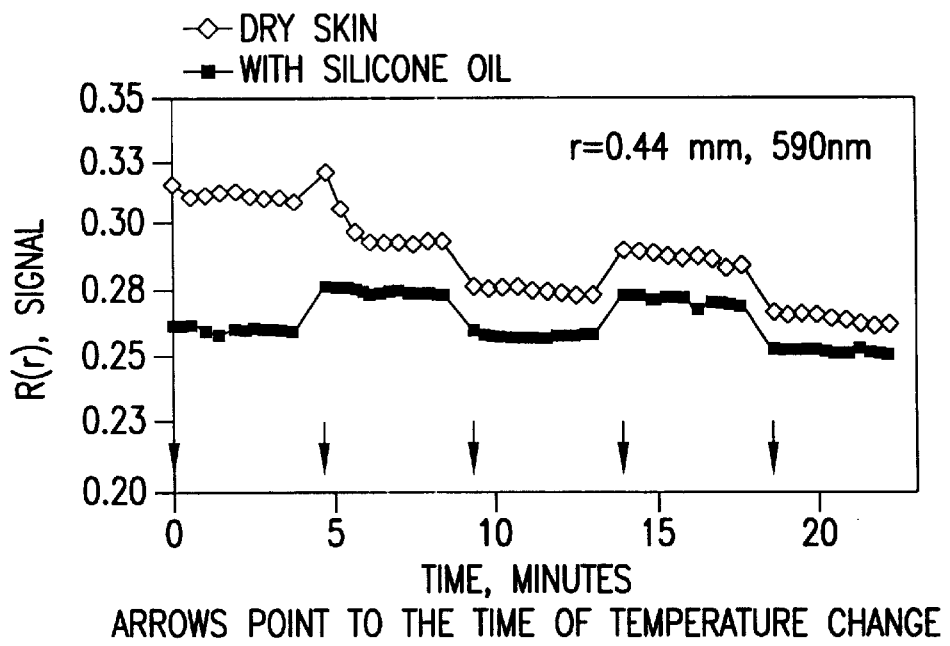
FIGS. 7A, 7B, 7C, and 7D are graphs illustrating change in diffuse reflectance in response to the skin temperature changes (indicated by arrows) in a temperature modulation experiment. The graphs show the effect of silicone oil as a coupling agent.
Figure 7B:
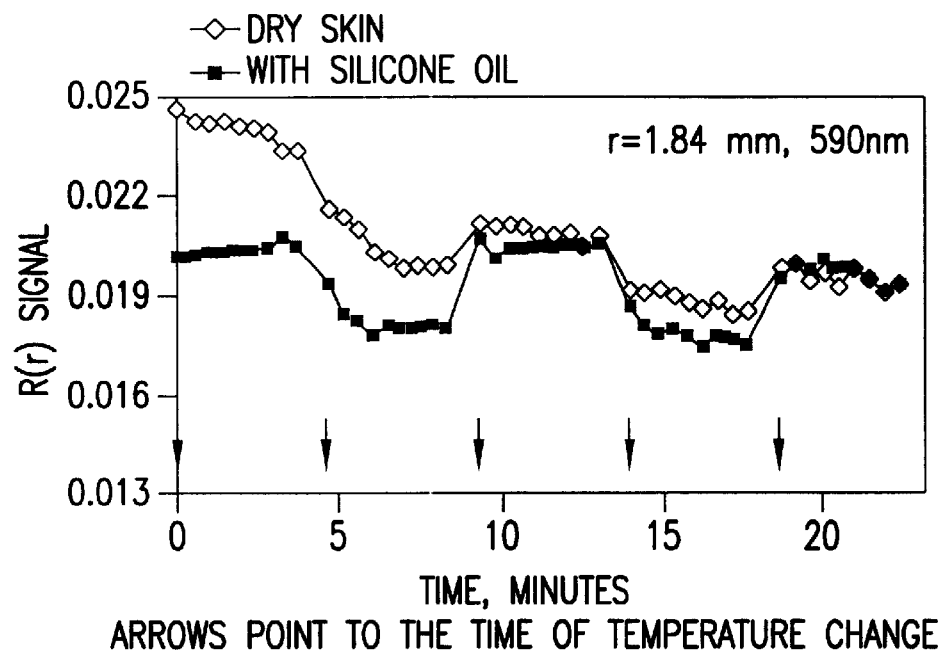
Figure 7C:
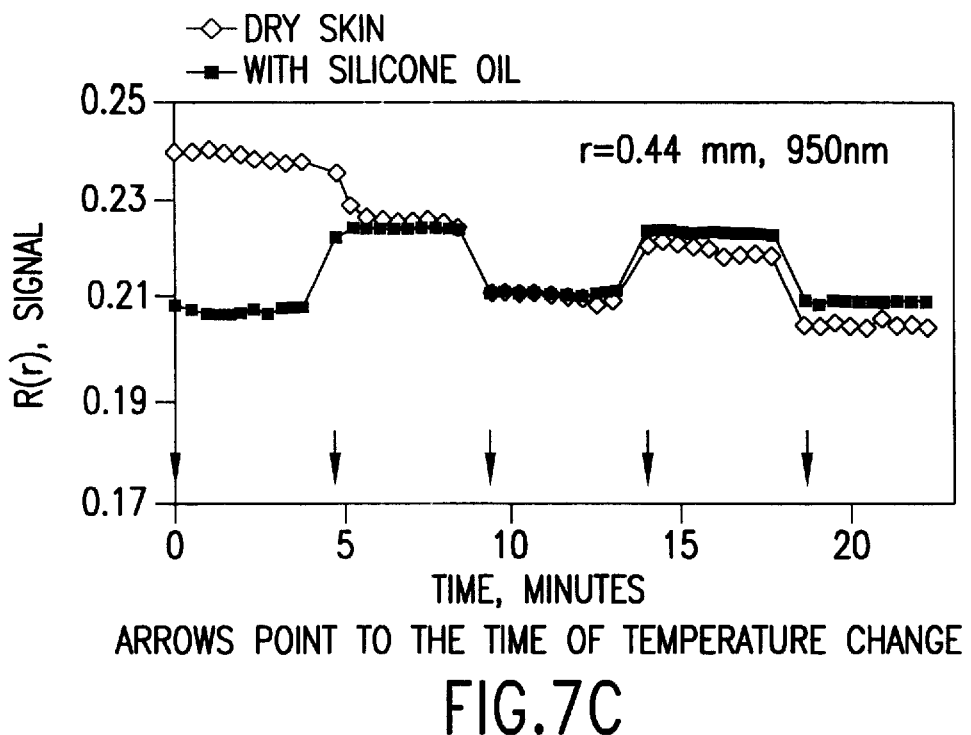
Figure 7D:
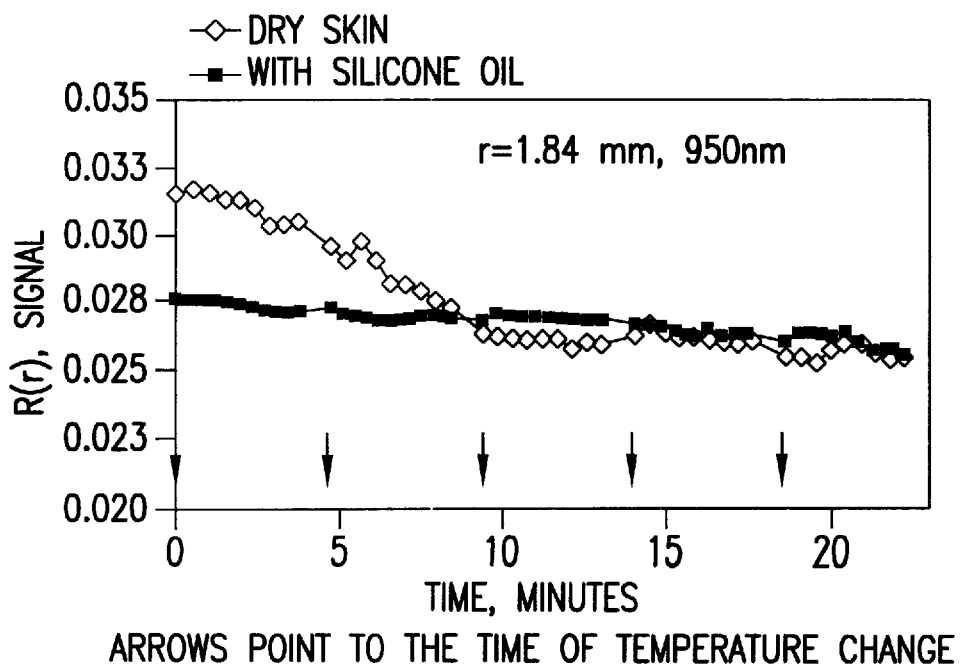
Figure 7E:
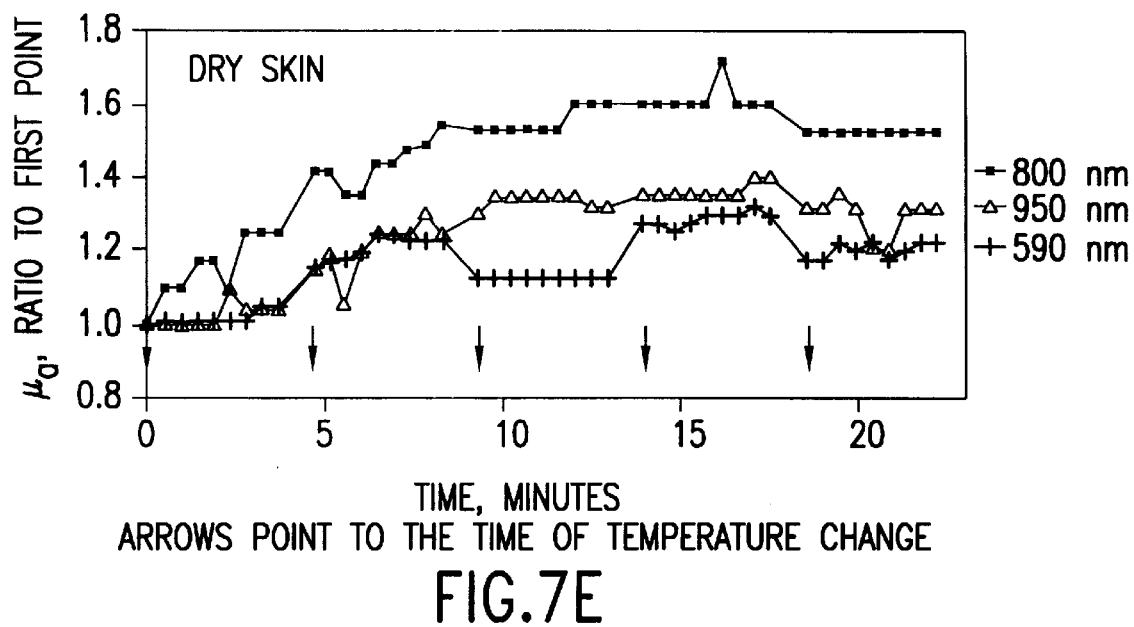
FIGS. 7E, 7F, 7G, and 7H are graphs illustrating the change of absorption coefficient (FIGS. 7E, 7G) and scattering coefficient (FIGS. 7F, 7H) in response to the skin temperature changes (indicated by arrows) in a temperature modulation experiment. The graphs show the effect of silicone oil as a coupling agent.
Figure 7F:
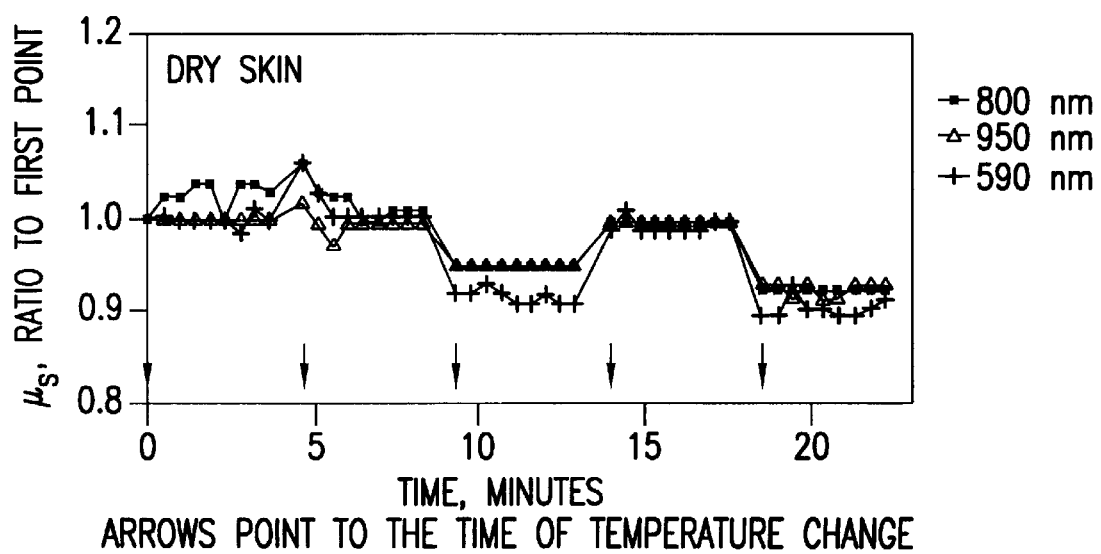
Figure 7G:
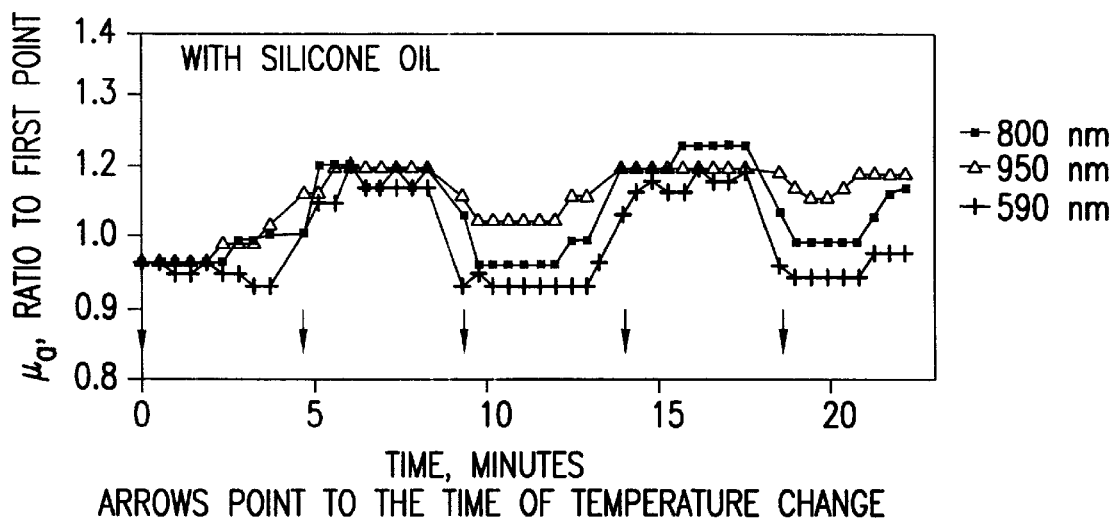
Figure 7H:
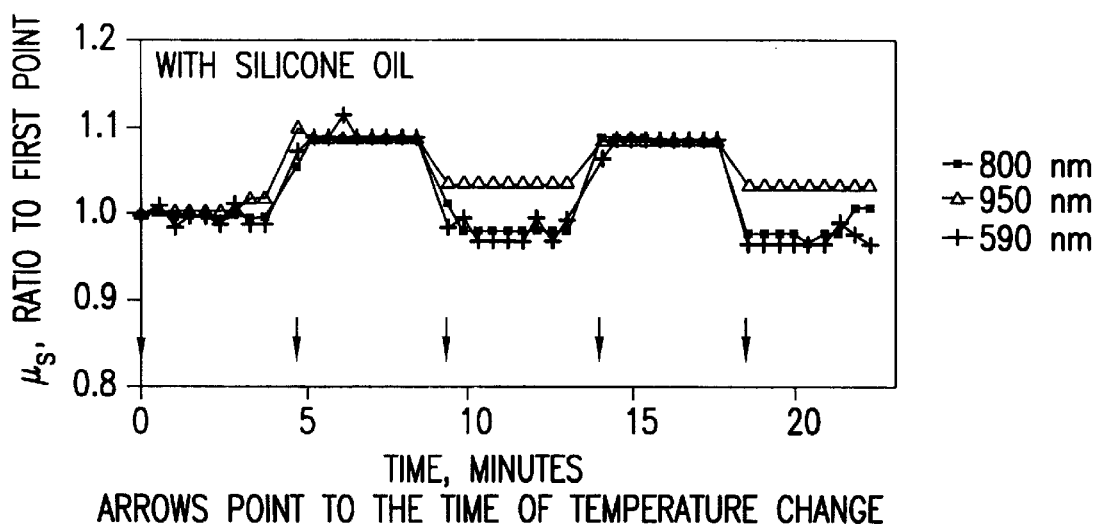

FIGS. 5A, 5B, 5C, and 5D display selected reflectance data of the first measurement (open diamonds) and the second measurement (solid squares). FIGS. 5A, 5B, 5C, and 5D show that in the measurement period (about 10 minutes), severe drift occurred at both detection distances (0.44 mm and 1.84 mm) and at both wavelengths (590 nm and 950 nm) when no oil was applied. However, after the application of the oil, all measured time dependent changes in signal, i. e., drifts, were significantly reduced. Similar effects were seen in the absorption coefficient data ($\mu_a$) at three selected wavelengths (590 nm, 800 nm, and 950 nm), as displayed in FIG. 5E. The value of $\mu_a$ was derived from the reflectance data, in the manner described in co-pending U.S. application Ser. No. 09/080,470. The first measurement (without coupling agent, solid symbols) registered 20% to 40% drift of the signal in 10 minutes, while the second measurement (with silicone oil, opened symbols) showed significant reduction of drift of the signal.

b. Effect of coupling agents other than silicone oil

The following materials were tested on the same subject in order to determine the effect of these materials on signal drift. All other measurement conditions and the method for applying the materials were the same as described above.

1) No coupling agent
2) De-ionized water
3) 25% Glycerol (Sigma Chemical Company, G-9012) in de-ionized water (completely soluble)
4) 50% Glycerol (Sigma Chemical Company, G-9012) in de-ionized water (completely soluble)
5) Mineral oil (Aldrich Chemical Company, Cat. No. 33-076-0)

The results are shown in FIGS. 6A, 6B, 6C, 6D, 6E, 6F, 6G, and 6H. It is clear that the use of mineral oil decreases drift significantly (FIGS. 6E, 6F, 6G, and 6H); it is not clear whether or not the application of coupling agents such as water and aqueous glycerol solutions reduces drift (FIGS. 6A, 6B, 6C, and 6D).

TABLE 2 summarizes the physical properties of several materials involved in this example.

TABLE 2

Properties of several materials (at 20° C., unless specified otherwise)

| Material | Density (kg/L) | Index of refraction | Viscosity (centipoises) | Thermal conductivity (milliwatt/cm/° C.) |
|---|---|---|---|---|
| Air | 0.0012 | 1.000 | 0.018 | 0.26 |
| Water | 0.998 | 1.333 | 1.002 | 6.0 |
| 25% Glycerol in water | 1.059 | 1.364 | 2.095 | 5.0 |
| 50% Glycerol in water | 1.127 | 1.398 | 6.05 | 4.2 |
| Glycerol | 1.263 | 1.474 | 1,487 | 3.9 |
| Silicone oil | 0.963 | 1.404 | 48* (25° C.) | 1.51** (50° C.) |
| Mineral oil | 0.862 | 1.476 | 34.5*** (40° C.) | 1.31** (50° C.) |

Example 3

This example demonstrates the reduction of drift and the improvement in temperature response under the condition of temperature modulation when a thermally conductive coupling agent is used in a non-invasive measurement. In the first measurement, a healthy male subject was tested with apparatus described in Example 1. No coupling agent was used. In the second measurement, an identical experiment was conducted with the same subject, with the exception that a coupling agent was applied. In both measurements, the measurement site was on the left forearm.

The coupling agent used was silicone oil (Aldrich Chemical Company, Cat. No. 14,615-3). The coupling agent had a refractive index of 1.404 and density of 0.963 kg/L.

The measurement temperature was first set at 22° C., and then switched between two constant settings, i. e., 22° C. and 38° C. Therefore, the temperature sequence was 22° C., 38° C., 22° C., 38° C. and 22° C. The temperature was switched at the time points indicated by small arrows in FIGS. 7A, 7B, 7C, 7D, 7E, 7F, 7G, and 7H. At each temperature, the signal was measured for about four minutes. Then, the temperature was switched to the next value in about one minute, and another signal was measured for about four minutes. Two measurements were performed. In the first measurement no coupling agent was used. Before the second measurement, one drop of the silicone oil was spread over the testing site of the left forearm of the subject, and another drop was spread over the tip 24 of the optical fiber and the temperature controlling element 50. When the optical probe was brought in contact with the skin, the oil formed a very thin layer between the skin and the probe, due to the low viscosity of the silicone oil.

FIGS. 7A, 7B, 7C, and 7D display selected reflectance data of the first measurement (open diamonds) and the second measurement (solid squares). FIGS. 7A, 7B, 7C, and 7D show that in the measurement period (about 10 minutes), severe drift occurred at both detection distances (0.44 mm and 1.84 mm) and at both wavelengths (590 nm and 950 nm) when no oil was applied. After the application of the oil, all measured changes in signal vs. time, i. e. drift was significantly lowered compared with the case of a measurement obtained with no coupling agent. In addition, sharper transitions from a state corresponding to one temperature to a state corresponding to another temperature were seen for data recorded when silicone oil was applied as a coupling agent. Similar effects were seen from the absorption and scattering coefficients data ($\mu_a$ and $\mu_s$) at three wavelengths (590 nm, 800 nm, and 950 nm), as displayed in FIGS. 7E, 7F, 7G, and 7H. The values of $\mu_a$ and $\mu_s$ were derived from reflectance data, in the manner described in co-pending U.S. application Ser. No. 09/080,470.

Example 2 and TABLE 2 show that the refractive index may be a factor in improving drift, but not an important one. Silicone oil and mineral oil are very effective in reducing background signal drift caused by the contact of the optical probe and the skin. The improvement in temperature response may be attributed to the much greater thermal conductivity of the oils as compared with that of air. However, thermal conductivity does not seem to be the only factor in determining drift. Other aqueous solutions with even better thermal conductivities, including water itself, 25% and 50% glycerol in water, did not reduce drift as well as did the oils.

In terms of the effect of index matching to the tissue, aqueous glycerol solutions were expected to be better than silicone oil or mineral oil, but they were not. The most effective coupling agents for reducing drift, silicone oil and mineral oil, show superior drift suppressing effect, even though they have a higher refractive index than that of the skin.

Aqueous solutions exhibit lack of stability due to evaporation of water, diffusion of the glycerol and/or water to the inner layers of skin, and migration of the skin components to the contact agents. In all cases, the instability is the result of composition change of the skin and of the thin layer of contact agent.

In contrast, silicone oil and mineral oil are extremely stable and do not bring about any transfer of material from or to the tissue. Furthermore, the much higher thermal conductivity of silicone oil and mineral oil (compared to air) makes them ideal for drift reduction.

As noted previously, reduction of drift is desirable in methods of determining the concentration of an analyte in a biological sample. Reduction of drift is also desirable for calibrating an optical instrument for a non-invasive optical measurement from a tissue of a body part. Calibration of an optical instrument for non-invasive glucose measurements can be achieved by performing a meal tolerance test or an oral glucose tolerance test. A test subject ingests a known amount of glucose after fasting for several hours. The concentration of glucose in blood is determined by a conventional invasive procedure, such as that involving collection of blood by means of a finger stick and determination of blood glucose level via a disposable test strip and an optical or electrochemical detector. The signal from the non-invasive instrument is processed and is correlated with the glucose concentration determined at the same time by the invasive procedure. The resultant plot of data collected by means of the non-invasive procedure vs. data collected by the invasive procedure is a calibration curve, which can be obtained by use of any appropriate fitting method, such as linear least squares fitting.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method for determining the concentration of analyte in a biological sample comprising the steps of:

(1) providing an optical measuring instrument that comprises at least one thermally controllable optical measuring element that comes into contact with a surface of said biological sample;

(2) applying an inert, thermally conductive, optically transparent coupling agent to said at least one optical measuring element or to said surface of said biological sample or both so that said coupling agent will be disposed at the interface of said surface of said biological sample and said at least one optical measuring element, said coupling agent having sufficiently high optical stability that the optical properties of said coupling agent do not change during optical measurements or during storage, said coupling agent having sufficiently high thermal conductivity to allow rapid, efficient heat transfer between said optical measuring element and said biological sample, said coupling agent having sufficiently high viscosity to prevent it from migrating from said interface, said coupling agent having sufficiently low viscosity to allow sufficient contact between said optical measuring element and said biological sample, said coupling agent having a refractive index higher than that of said biological sample over the temperature range of a measurement;

(3) measuring at least one optical property of said biological sample by means of said at least one optical measuring element; and (4) correlating the at least one optical property of said biological sample with the concentration of said analyte in said biological sample.

2. The method of claim 1, further including the step of controlling the temperature of said biological sample, whereby said at least one optical property of said biological sample is measured at a given depth from the surface of said biological sample.

3. The method of claim 2, wherein said depth from the surface of said biological sample is less than 3 mm.

4. The method of claim 2, wherein said depth from the surface of said biological sample is less than 2 mm.

5. The method of claim 1, wherein said measuring step is carried out at a plurality of wavelengths.

6. The method of claim 1, wherein said coupling agent is thermally stable at temperatures ranging from 10° C. to 45° C.

7. The method of claim 1, wherein said coupling agent is inert to oxygen at temperatures ranging from 10° C. to 45° C.

8. The method of claim 1, wherein said coupling agent has a thermal conductivity greater than 1 milliwatt/cm/° C.

9. The method of claim 1, wherein said coupling agent has sufficient viscosity that it will not migrate from said optical measuring element.

10. The method of claim 9, wherein said coupling agent has a viscosity in the range of from about 10 centipoises to about 100,000 centipoises.

11. The method of claim 1, wherein said coupling agent does not diffuse into said biological sample.

12. A method for measuring the concentration of an analyte in a tissue of a body part comprising the steps of:

(1) providing an optical measuring instrument that comprises at least one thermally controllable optical measuring element that comes into contact with the surface of said tissue;

(2) applying an inert, thermally conductive, optically transparent coupling agent to said at least one optical measuring element or to the surface of said tissue or both so that said coupling agent will be disposed at the interface of said surface of said tissue and said at least one optical measuring element, said coupling agent having sufficiently high optical stability that the optical properties of said coupling agent do not change during optical measurements or during storage, said coupling agent having sufficiently high thermal conductivity to allow rapid, efficient heat transfer between said optical measuring element and said tissue, said coupling agent having sufficiently high viscosity to prevent it from migrating from said interface, said coupling agent having sufficiently low viscosity to allow sufficient contact between said optical measuring element and said tissue, said coupling agent having a refractive index higher than that of said tissue over the temperature range of a measurement;

(3) inducing a change in the concentration of said analyte in said tissue over a defined period of time;

(4) measuring the change in at least one optical property of said tissue by means of said at least one optical measuring element during said defined period of time;

(5) determining the change in the concentration of said analyte in said tissue by means of a reference method that involves taking a sample from said tissue for analysis during said defined period of time;

(6) correlating the change in said at least one optical property of said tissue with the change in the concentration of the analyte in said tissue to derive calibration data; and (7) using said calibration data to determine the concentration of said analyte in said tissue.

13. The method of claim 12, further including the step of controlling the temperature of said tissue, whereby said at least one optical property of said biological sample is measured at a given depth from the surface of said biological sample.

14. The method of claim 13, wherein said depth from the surface of said tissue is less than 3 mm.

15. The method of claim 13, wherein said depth from the surface of said tissue is less than 2 mm.

16. The method of claim 12, wherein said measuring step is carried out at a plurality of wavelengths.

17. The method of claim 12, wherein said coupling agent is thermally stable at temperatures ranging from 10° C. to 45° C.

18. The method of claim 12, wherein said coupling agent is inert to oxygen at temperatures ranging from 10° C. to 45° C.

19. The method of claim 12, wherein said coupling agent has a thermal conductivity greater than 1 milliwatt/cm/° C.

20. The method of claim 12, wherein said coupling agent has sufficient viscosity that it will not migrate from said optical measuring element.

21. The method of claim 20, wherein said coupling agent has a viscosity in the range of from about 10 centipoises to about 100,000 centipoises.

22. The method of claim 12, wherein said coupling agent does not diffuse into said biological sample.

* * * * *